US012042470B2

(12) United States Patent
Nishio et al.

(10) Patent No.: US 12,042,470 B2
(45) Date of Patent: Jul. 23, 2024

(54) DRUG DISPENSING DEVICE

(71) Applicant: YUYAMA MFG. CO., LTD., Osaka (JP)

(72) Inventors: Masashi Nishio, Osaka (JP); Masato Suzuki, Osaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 1004 days.

(21) Appl. No.: 16/975,136

(22) PCT Filed: Jun. 25, 2019

(86) PCT No.: PCT/JP2019/025244
§ 371 (c)(1),
(2) Date: Aug. 24, 2020

(87) PCT Pub. No.: WO2020/004423
PCT Pub. Date: Jan. 2, 2020

(65) Prior Publication Data

US 2021/0093513 A1 Apr. 1, 2021

(30) Foreign Application Priority Data

Jun. 26, 2018 (JP) ................................ 2018-120763

(51) Int. Cl.
*B65B 37/08* (2006.01)
*A61J 7/00* (2006.01)
*G16H 20/13* (2018.01)

(52) U.S. Cl.
CPC ............. *A61J 7/0084* (2013.01); *B65B 37/08* (2013.01); *G16H 20/13* (2018.01)

(58) Field of Classification Search
CPC .......... A61J 7/0084; A61J 1/03; A61J 7/0076; B65B 37/08; G16H 20/13; G07F 13/10; G07F 11/44; G07F 17/0092
See application file for complete search history.

(56) References Cited

U.S. PATENT DOCUMENTS 7,584,018 B2 * 9/2009 Shows .................... G07F 11/54 700/242
8,038,016 B2 * 10/2011 Yuyama ............. G07F 17/0092 221/9

(Continued)

FOREIGN PATENT DOCUMENTS

AU 2016362656 A1 6/2018
CA 2962284 A1 6/2016

(Continued)

OTHER PUBLICATIONS

Office Action in CA Application No. 3,093,894, dated Jun. 29, 2022, 4pp.

(Continued)

*Primary Examiner* — Patrick H Mackey
(74) *Attorney, Agent, or Firm* — HAUPTMAN HAM, LLP

(57) ABSTRACT

A drug cassette including a solid-preparation receiving portion, a lid member, lid locking means configured to hold the lid member in a locked state provided to the drug cassette, a cassette placement portion configured to place the drug cassette, removing/locking means and lid locking operation means configured to prevent removal of the drug cassette, provided to the cassette placement portion. After the lid locking means is brought into an unlocking state by the lid locking operation means, until the lid locking operation means operates in accordance with an operation by an operator so that the lid locking means is locked, the unlocking state of the lid locking means is maintained. After the lid locking means is locked by the lid locking operation means, the removing/locking means is cancelled, and the drug cassette is brought into a state of being removable from the cassette placement portion.

6 Claims, 18 Drawing Sheets

11
10
73
55
53
38
38

(56) References Cited

U.S. PATENT DOCUMENTS

| | | | |
|---|---|---|---|
| 9,770,389 | B2 | 9/2017 | Koike et al. |
| 9,977,871 | B2 * | 5/2018 | Schultz ............... G07F 17/0092 |
| 10,441,510 | B2 * | 10/2019 | Omura .................. A61J 7/0007 |
| 2006/0167586 | A1 | 7/2006 | Kobayashi et al. |
| 2012/0042609 | A1 | 2/2012 | Inoue et al. |
| 2015/0014343 | A1 | 1/2015 | Koike |
| 2016/0311640 | A1 * | 10/2016 | Moore ................. B65H 55/046 |
| 2016/0331640 | A1 * | 11/2016 | Koike ....................... A61J 3/00 |
| 2018/0105300 | A1 | 4/2018 | Mitani et al. |
| 2018/0369071 | A1 * | 12/2018 | Koike ................... A61J 7/0076 |
| 2022/0401307 | A1 * | 12/2022 | Bijlsma ................... B65B 55/24 |

FOREIGN PATENT DOCUMENTS

| | | | |
|---|---|---|---|
| CA | 2982433 | A1 | 10/2016 |
| CN | 106794116 | A | 5/2017 |
| CN | 107530225 | A | 1/2018 |
| JP | 2006206090 | A | 8/2006 |
| KR | 1020170084041 | A | 7/2017 |
| WO | 2010110360 | A1 | 9/2010 |
| WO | 2013118838 | A1 | 8/2013 |
| WO | 2016067929 | A1 | 5/2016 |
| WO | 2016167148 | A1 | 10/2016 |

OTHER PUBLICATIONS

Office Action in CN Application No. 201980015613.3, mailed Jun. 6, 2022, 22pp.

Office Action in KR Application No. 10-2021-7001937, dated Dec. 9, 2022, 10pp.

International Search Report in PCT/JP2019/025244, mailed Sep. 24, 2019. 4pp.

Extended European Search Report in EP Application No. 19825391.6, dated Mar. 3, 2022. 9pp.

Office Action in EP Application No. 19825391.6, dated Mar. 6, 2024, 6pp.

* cited by examiner

FIG. 24

QUANTITY OF EMITTED LIGHT ON OUTER SIDE (D/A): DARK → BRIGHT

QUANTITY OF EMITTED LIGHT ON INNER SIDE (D/A): DARK → BRIGHT

| | −3 | −2 | −1 | ±0 | +1 | +2 | +3 | +4 | +5 | +6 |
|---|---|---|---|---|---|---|---|---|---|---|
| −3 | 1 | 3 | 7 | 13 | 21 | 31 | 43 | 57 | 73 | 91 |
| −2 | 2 | 4 | 8 | 14 | 22 | 32 | 44 | 58 | 74 | 92 |
| −1 | 5 | 6 | 9 | 15 | 23 | 33 | 45 | 59 | 75 | 93 |
| ±0 | 10 | 11 | 12 | 16 | 24 | 34 | 46 | 60 | 76 | 94 |
| +1 | 17 | 18 | 19 | 20 | 25 | 35 | 47 | 61 | 77 | 95 |
| +2 | 26 | 27 | 28 | 29 | 30 | 36 | 48 | 62 | 78 | 96 |
| +3 | 37 | 38 | 39 | 40 | 41 | 42 | 49 | 63 | 79 | 97 |
| +4 | 50 | 51 | 52 | 53 | 54 | 55 | 56 | 64 | 80 | 98 |
| +5 | 65 | 66 | 67 | 68 | 69 | 70 | 71 | 72 | 81 | 99 |
| +6 | 82 | 83 | 84 | 85 | 86 | 87 | 88 | 89 | 90 | 100 |

STANDARD RANGE

ADDITIONAL RANGE

DRUG DISPENSING DEVICE

RELATED APPLICATIONS

The present application is National Phase of International Application Number PCT/JP2019/025244 filed Jun. 25, 2019, which claims priority of Japanese Application No. 2018-120763, filed Jun. 26, 2018.

TECHNICAL FIELD

This disclosure relates to a drug dispensing device which has a function to dispense a predetermined amount of solid drugs.

BACKGROUND ART

Ina hospital or a pharmacy, tablets or the like prepared for a patient are bottled in a vial or the like and handed to the patient or the like. Hitherto, an operation of bottling a drug into a vial has been manually performed by a pharmacy worker such as a pharmacist. That is, a pharmacist selects a drug bottle containing a drug based on a prescription among a plurality of kinds of drugs in stock, takes out the drug from the drug bottle, counts the number of the drug, bottles the drug into the vial, and hands the vial to a patient or the like.

However, the operation of selecting a drug bottle and further manually filling a drug from the drug bottle into a vial is an operation which requires time and effort. In view of such a disadvantage, in Patent Literature 1, there is proposed a drug dispensing device configured to automatically perform a series of operations from selecting a drug to filling the drug into a vial. According to the drug dispensing device disclosed in Patent Literature 1, various kinds of drugs to be dispensed are stored in a plurality of drug cassettes. Incidentally, when a drug contained in a drug cassette is emptied, a pharmacy worker takes out a drug cassette from a drug dispensing device and replenishes the drug cassette with a drug by own hand. At the time of replenishment, there is a risk in that the pharmacy worker replenishes the drug cassette with an incorrect drug.

A measure for solving this problem is disclosed in, for example, Patent Literature 2. According to a drug dispensing device disclosed in Patent Literature 2, a lid is provided to a drug cassette, and a mechanism configured to lock the lid is further provided. Moreover, the drug dispensing device includes a placement table that is to be used at the time of replenishing the drug cassette with a drug. An unlocking device configured to unlock the lid is provided to the placement table. The drug dispensing device disclosed in Patent Literature 2 further includes an optical scanner.

According to the drug dispensing device disclosed in Patent Literature 2, a code provided to the drug bottle is read with the optical scanner. Then, when the drug contained in the drug bottle is the drug to be stored in the drug cassette, the unlocking device operates to allow the lid of the drug cassette to be opened.

CITATION LIST

Patent Literature

[PTL 1] WO 2010/110360 A1
[PTL 2] WO 2016/67929 A1
[PTL 3] WO 2013/118838 A1

SUMMARY OF INVENTION

Technical Problem

According to the related-art drug dispensing devices, the lid of the drug cassette does not open when the drug is incorrect. Therefore, a risk of replenishing the drug cassette with an incorrect drug is low. Incidentally, in Patent Literature 2, there is no description as to the operation to be performed when the lid of the drug cassette is once closed. For example, there is a case in which, even after replenishing the drug cassette with a drug and closing the lid, a pharmacy worker regrets that a larger amount of a drug should have been replenished. In contrast, there is also a case in which the drug cassette is filled with an excessive amount of a drug. In Patent Literature 2, there is no disclosure as to a countermeasure against such a case.

This disclosure focuses on the above-mentioned problems of the related art, and has an object to develop a drug dispensing device capable of re-opening a lid of a drug cassette even after the lid is closed.

Solution to Problem

In order to solve the above-mentioned problems, according to an aspect of this disclosure, there is provided a drug dispensing device, including a plurality of drug cassettes, the drug dispensing device being capable of taking out a desired number of solid drugs from the drug cassette. The drug cassette includes: a solid-preparation receiving portion configured to receive a solid drug; and a lid member configured to close the solid-preparation receiving portion. The drug cassette includes lid locking means configured to hold the lid member in a locked state. The drug dispensing device includes a cassette placement portion configured to place the drug cassette. The drug dispensing device includes: removing/locking means configured to hold the drug cassette on the cassette placement portion and prevent removal of the drug cassette; and lid locking operation means configured to operate the lid locking means. The lid locking operation means is capable of bringing the lid locking means into a lockable state and an unlocking state, and after the lid locking means is brought into the unlocking state by the lid locking operation means, the unlocking state of the lid locking means is maintained until the lid locking operation means operates in accordance with an operation by an operator so that the lid locking means is brought into the lockable state. After the lid locking means is brought into the lockable state by the lid locking operation means, or when a condition for bringing the lid locking means into the lockable state is satisfied, the removing/locking means is cancelled automatically or through a predetermined operation so that the drug cassette is brought into a state of being removable from the cassette placement portion.

Here, the locked state of the lid member corresponds to a state in which the lid member does not open. The lid member in the locked state cannot be opened unless a tool is used or a complicated operation is performed. The lockable state of the lid locking means corresponds to a state in which the lid member can be brought into the locked state of the lid member when the lid member is in a predetermined position or posture. The unlocking state of the lid locking means corresponds to a state in which the lid member automatically opens or in which the lid member can be opened by moving the lid member by hand. Moreover, a case of enabling the lid member to be opened through a simple operation is also included in the unlocking state.

In the above-mentioned aspect of this disclosure, it is preferred that the drug dispensing device further include an operating portion, and that, when an operator performs a particular operation to the operating portion, the lid locking operation means operate, and the removing/locking means be cancelled, thereby allowing the drug cassette to be removable from the cassette placement portion.

In order to solve a similar problem, according to another one aspect of this disclosure, there is provided a drug dispensing device, including a plurality of drug cassette, the drug dispensing device being capable of taking out a desired number of solid drugs from the drug cassette. The drug cassette includes: a solid-preparation receiving portion configured to receive a solid drug; a lid member configured to close the solid-preparation receiving portion; and lid locking means configured to hold the lid member in a locked state. The drug dispensing device includes lid locking operation means configured to operate the lid locking means, and the lid locking operation means is configured to bring the lid locking means into a lockable state in accordance with an operation by an operator.

In each of the above-mentioned aspects, in the drug dispensing device further including: a cassette placement portion configured to place the drug cassette; removing/locking means configured to hold the drug cassette on the cassette placement portion and prevent removal of the drug cassette; and lid locking operation means configured to operate the lid locking means, it is preferred that the lid locking operation means be capable of bringing the lid locking means into a lockable state and an unlocking state, that the drug dispensing device include an operating portion, and that, through the operating portion, under a condition in which operator information, a date, and any one of drug serial number information, the number of replenishment, and an expiration date are input, the lid locking operation means operate to bring the lid locking means into the lockable state from the unlocking state, and the removing/locking means be cancelled.

In the above-mentioned aspect, it is preferred that the drug dispensing device further include an inside of the drug dispensing device and/or a storage configured to communicate with the inside of the drug dispensing device, and that the operator information, the date, and drug-cassette identification information be associated with any one of the drug serial number information and the expiration date and be stored in the storage.

Advantageous Effects of Invention

In the drug dispensing device according to this disclosure, the lid locking operation means operates in accordance with an operation by an operator. With the drug dispensing device according to this disclosure, the unlocking state of the lid locking means is maintained until the lid locking means is brought into the unlocking state in accordance with an operation by an operator. Therefore, the lid can be re-opened even after the lid is once closed.

BRIEF DESCRIPTION OF DRAWINGS

FIG. 24 is a table for showing a procedure of carrying out light-quantity adjustment for the drug counting means.

DESCRIPTION OF EMBODIMENTS

Figure 1:
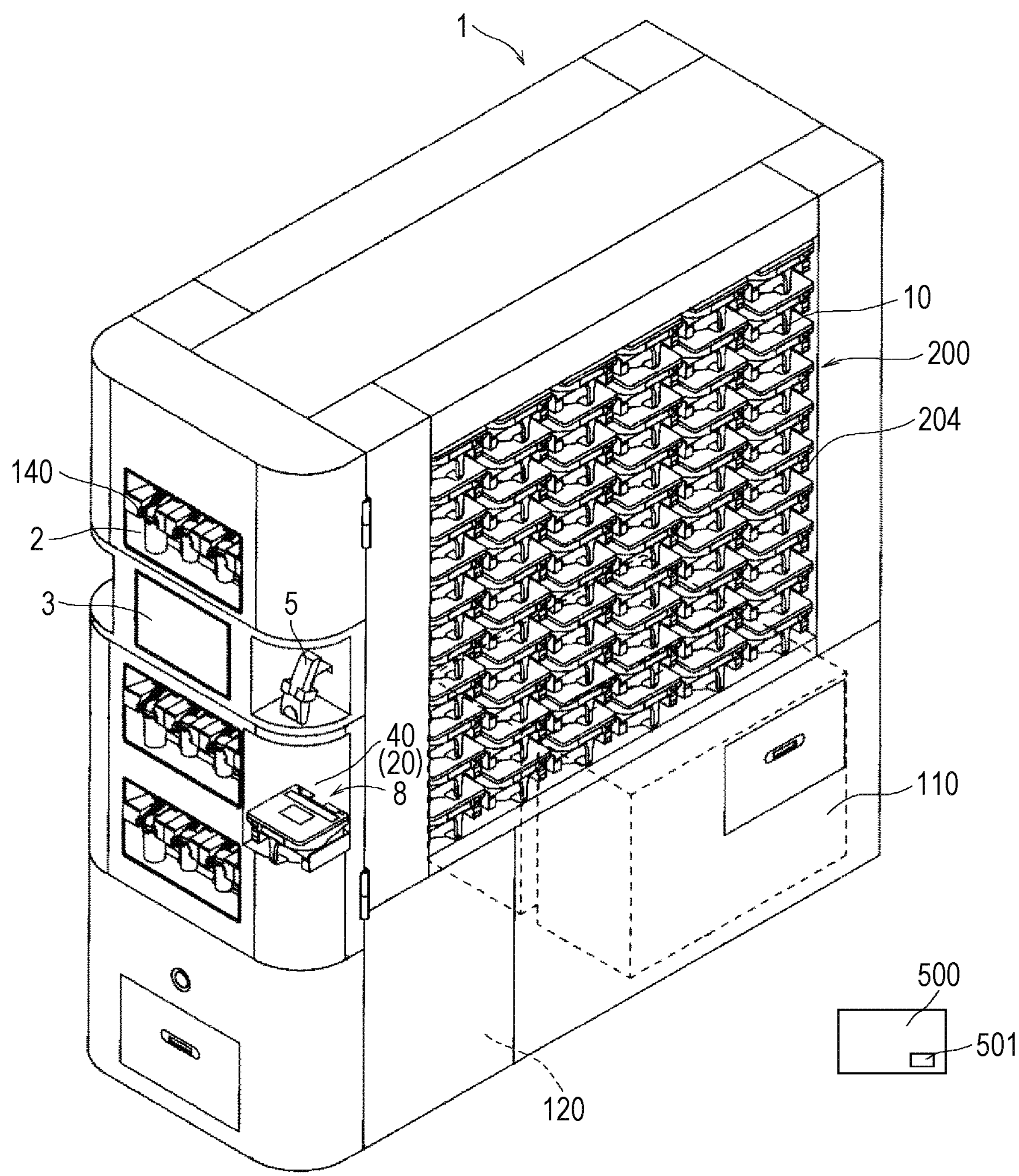
FIG. 1 is a perspective view for illustrating a drug dispensing device according to an embodiment of this disclosure.

Now, an embodiment of this disclosure is further described. First, an outline of a drug dispensing device 1 is described. The drug dispensing device 1 according to this embodiment has a function to select a specified solid drug from a group of solid drugs of various kinds based on input prescription information and fill the selected solid drug into a vial. The solid drug is a generic term of a tablet, a capsule, and the like. In the following, description is made of a case of using a tablet. However, the drug dispensing device 1 according to this embodiment is not limited to the usage for dispensing a tablet, and can be used for dispensing a solid drug other than the tablet. The drug dispensing device 1 according to this embodiment includes a storage rack 2 and a touch-panel display 3, which are provided on a front side. Moreover, a control device (not shown) is provided on a back side of the touch-panel display 3. An optical scanner 5 and a cassette placement portion 8 are further provided on the front side of the drug dispensing device 1.

The drug dispensing device 1 includes a vial supplying device 110, a labeling device 120, and a vial conveying device 130 (FIG. 16 and FIG. 17), which are provided inside the drug dispensing device 1. An inside and an outside of the drug dispensing device 1 communicate with each other through a bottle delivery port 140. The drug dispensing device 1 further includes a container arrangement portion 200 on a side.

A large number of drug-cassette mounting portions 204 are provided to the container arrangement portion 200. Further, drug cassettes 10 are mounted to the drug-cassette mounting portions 204, respectively. In the container arrangement portion 200, the plurality of drug cassettes 10 are arranged in a matrix pattern. Different kinds of tablets are provided in the drug cassettes 10, respectively.

The vial supplying device 110 also has a function to store a plurality of vials. The touch-panel display 3 has a function as a display device and a function as an input device (operating portion). The optical scanner 5 is capable of reading symbols to be read by an optical scanner, such as a barcode or a two-dimensional code. The control device (not shown) is configured to control operations of the various devices provided to the drug dispensing device 1 based on input information from the touch-panel display 3 or the like.

When the drug dispensing device 1 dispenses a drug, first, the optical scanner 5 scans a symbol given to a prescription to acquire prescription information. Alternatively, when a keyboard and/or a mouse is connected to the drug dispensing device 1, the drug dispensing device 1 can receive input of prescription information via the keyboard and/or the mouse. Further, when the drug dispensing device 1 is connected to a network, the drug dispensing device 1 can receive input of prescription information via the network.

When the drug dispensing device 1 receives the input of prescription information and receives input of a drug dispensing instruction from a pharmacy worker, first, the vial supplying device 110 supplies a vial to the labeling device 120. Then, the labeling device 120 prints a label based on the input prescription information and affixes the label to the vial. After that, the vial conveying device 130 conveys the vial, to which the label has been affixed, to the vicinity of the drug cassette 10 accommodating the prescribed drug. Then, the drug cassette 10 dispenses a prescribed amount of the prescribed drug to the vial. After the prescribed drug is filled into the vial, the vial conveying device 130 conveys the vial to the bottle delivery port 140. Then, the vial delivered to the bottle delivery port 140 is taken out by a pharmacy worker such as a pharmacist or a technician.

Figure 5:
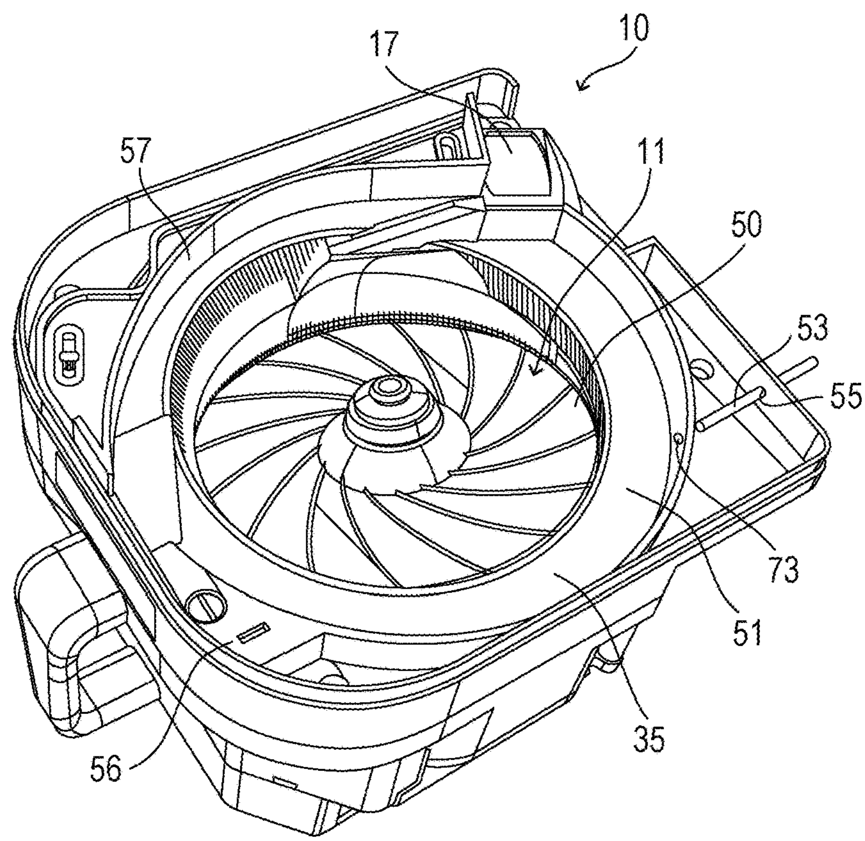
FIG. 5 is a perspective view for illustrating the drug cassette of FIG. 2 in a state in which the lid member is opened and an inside of the drug cassette is observed.
Figure 6:
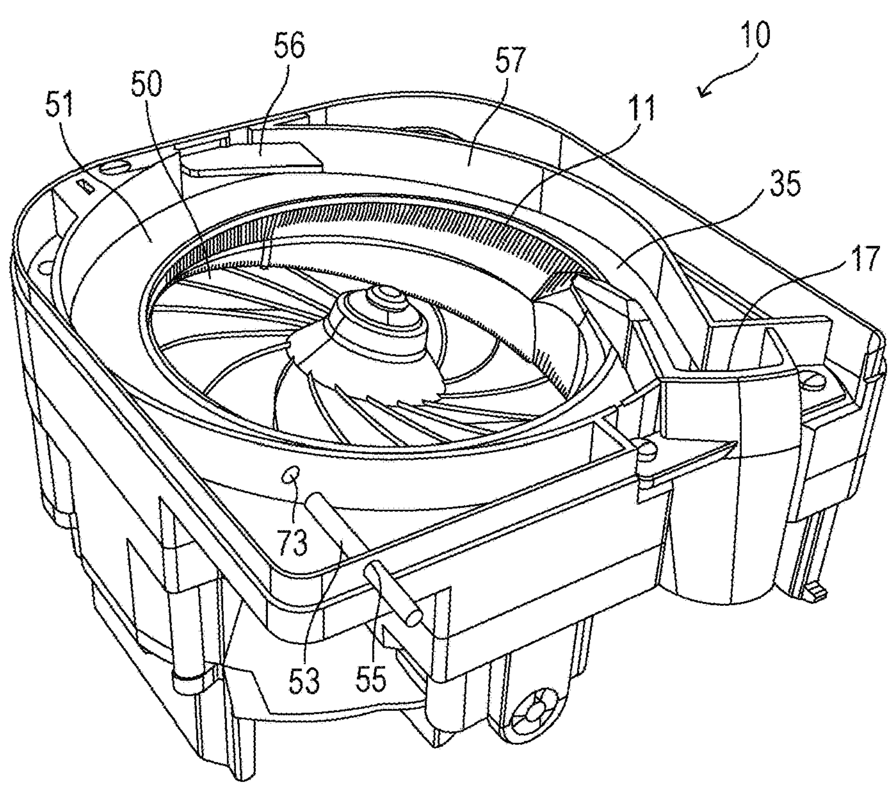
FIG. 6 is a perspective view for illustrating the drug cassette of FIG. 2 in a state in which the lid member is opened and the inside of the drug cassette is observed from a direction different from that of FIG. 5.

Next, description is made of devices mounted to the drug dispensing device 1. (Drug Cassette 10) As illustrated in FIG. 5 and FIG. 6, the drug cassette 10 includes a solid-preparation receiving portion 11 configured to receive a tablet, and is configured to deliver a desired number of tablets received in the solid-preparation receiving portion 11. Moreover, as illustrated in FIG. 2, FIG. 3, FIG. 8, and FIG. 9, a lid member 12 configured to cover the solid-preparation receiving portion 11 is provided to the drug cassette 10. Mainly with reference to FIG. 5 and FIG. 6, description is made of the basic structure of the drug cassette 10. FIG. 5 and FIG. 6 are illustrations in which the lid member 12 configured to cover an upper part of the drug cassette 10 is omitted. The drug cassette 10 is adaptable to tablets and capsules having various shapes and structure, and is capable of delivering the tablets and capsules one after another or in groups. That is, the drug cassette 10 includes mode changing means configured to change modes such that tablets can be smoothly delivered depending on the shape of the tablets. Specifically, the drug cassette 10 increases or decreases the size of a dispensing passage for allowing passage of tablets to limit the shape of tablets that may pass through the dispensing passage so as to be adaptable to tablets having a plurality of shapes and structures, thereby being adaptable to a plurality of kinds of tablets.

As illustrated in FIG. 5 and FIG. 6, the drug cassette 10 includes the solid-preparation receiving portion 11 configured to receive a large number of tablets, a first rotary body (hereinafter sometimes referred to as "inner rotary body" or "inner ring") 50, and a second rotary body (hereinafter sometimes referred to as "outer rotary body" or "outer ring") 51. The first rotary body 50 is a disc-shaped member forming a bottom surface of the solid-preparation receiving portion 11. A rotation axis of the first rotary body 50 is inclined by a predetermined angle with respect to a vertical direction, and an upper surface of the first rotary body 50 is inclined by a predetermined angle with respect to a horizontal plane. Moreover, radial ribs are formed at predetermined intervals on the upper surface of the first rotary body 50. The first rotary body 50 is rotatably supported by a housing of the drug cassette 10 and is rotated by a motor (not shown). Moreover, the first rotary body 50 is configured to rise and fall.

The second rotary body 51 is a hollow ring-shaped member arranged around the first rotary body 50 in plan view. The second rotary body 51 is provided on an upper portion side of the solid-preparation receiving portion 11. An upper end portion of the first rotary body 50 described above is located on the same horizontal plane as the second rotary body 51. The second rotary body 51 is also rotatably supported by the housing of the drug cassette 10 and is rotated by a motor (not shown).

Figure 7:
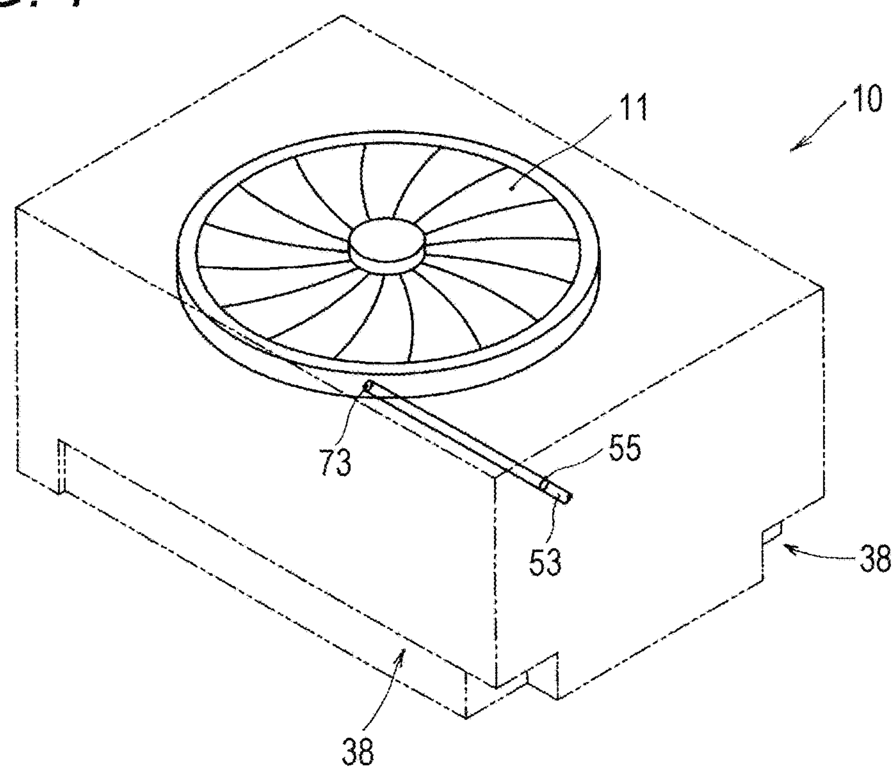
FIG. 7 is an explanatory view for illustrating a relationship between the drug cassette and a drug detection sensor.

Apart of the second rotary body 51 continues to a tablet delivery port 17 configured to deliver tablets from the solid-preparation receiving portion 11. The tablets are conveyed to the tablet delivery port 17 through the rotation of the second rotary body 51. Thus, the upper portion of the second rotary body 51 forms a part of a dispensing passage 35 for allowing the tablets to pass therethrough. Further, in this embodiment, on the dispensing passage 35 formed of the second rotary body 51, there are arranged a height regulating member 56 and a width regulating member 57. Moreover, in this embodiment, an overflow sensor (drug detection sensor) 53, which is configured to detect whether or not a tablet is present on the dispensing passage 35 formed of the second rotary body 51, is provided to a moving head 400 described later. The overflow sensor 53 is an optical sensor including a light-emitting portion and a light-receiving portion. The overflow sensor 53 is configured to detect the presence or absence of a tablet by emitting light through a hole 73 that faces the dispensing passage 35 and then receiving the light reflected from the tablet at the light-receiving portion. In FIG. 5, FIG. 6, and FIG. 7, a schematic illustration is given of a state in which the light radiated by the light-emitting portion of the overflow sensor 53 passes through a hole 55 formed in a contour body of the drug cassette 10 (or a state in which the light reflected from the tablet passes through the hole 55).

The height regulating member 56 described above is located above the second rotary body 51 and is configured to regulate a height from a conveyance surface of the second rotary body 51. The height regulating member 56 is configured to regulate a height of an object that passes through that part. The height regulating member 56 is configured to regulate the size of tablets in the height direction, which can be conveyed to the tablet delivery port 17 by the second rotary body 51.

Meanwhile, the width regulating member 57 protrudes from the side of the second rotary body 51 to the region of the second rotary body 51 (dispensing passage 35) and is configured to temporarily narrow the width of the dispensing passage 35 of the second rotary body 51. The width regulating member 57 is configured to regulate the size of the tablets in the width direction, which can be conveyed to the tablet delivery port 17 by the second rotary body 51. Therefore, in the drug cassette 10, among tablets placed on the second rotary body 51, only tablets which fit to the height regulated by the height regulating member 56 described above and the width regulated by the width regulating member 57 described above are dispensed through the tablet delivery port 17. Thus, in the drug cassette 10, when the height and the width fit to a height and a width for one tablet received in the solid-preparation receiving portion 11, the tablet can be dispensed one after another.

In the drug cassette 10 of this embodiment, the first rotary body (inner rotary body) 50 and the second rotary body (outer rotary body) 51 are rotated by the motors (not shown). Moreover, the first rotary body 50 is configured to rise and fall in the solid-preparation receiving portion 11. At the time of delivering the tablets stored in the drug cassette 10, the first rotary body 50 and the second rotary body 51 are rotated. When the first rotary body 50 is rotated in a forward direction, the tablets received in the solid-preparation receiving portion 11 are delivered from the first rotary body 50 to the second rotary body 51. Moreover, when the second rotary body 51 is rotated in a forward direction, the tablets on the second rotary body 51 are conveyed toward the tablet delivery port 17.

However, in this embodiment, the height and the width of the dispensing passage 35 for tablets are restricted by the height regulating member 56 and the width regulating member 57. Therefore, among the tablets conveyed by the second rotary body 51, tablets stacked in the height direction are brought into contact with the height regulating member 56 and returned to the solid-preparation receiving portion 11. Moreover, among the tablets conveyed by the second rotary body 51, solid preparations conveyed while being arranged side by side in the width direction are brought into contact with the width regulating member 57 and returned to the solid-preparation receiving portion 11.

In the drug cassette 10 of this embodiment, the first rotary body 50 provided on the inner side slowly rises while rotating in the forward direction. The group of tablets received in the solid-preparation receiving portion 11 rise while rotating along with the rotation and the rise of the first rotary body 50. Then, when the height of an upper portion of the group of tablets reaches the height of the second rotary body 51 provided on the outer side, and the tablets are detected by the overflow sensor 53, the rise of the first rotary body 50 is stopped, and the first rotary body 50 rotates in the forward direction at that height to supply the tablets to the second rotary body 51 provided on the outer side. The second rotary body 51 provided on the outer side also rotates in the forward direction, and the tablets on the second rotary body 51 are conveyed toward the tablet delivery port 17.

Figure 2:
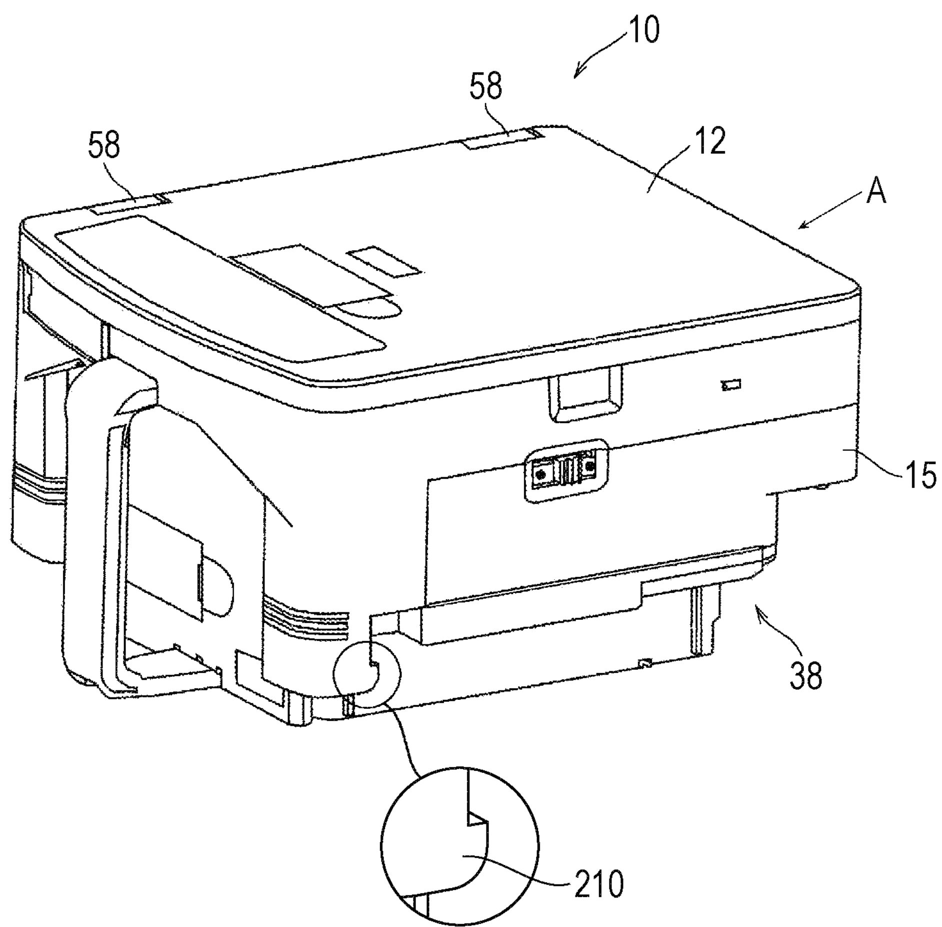
FIG. 2 is a perspective view for illustrating a drug cassette provided to the drug dispensing device of FIG. 1, and is an illustration of a state in which a lid member is closed.
Figure 8:
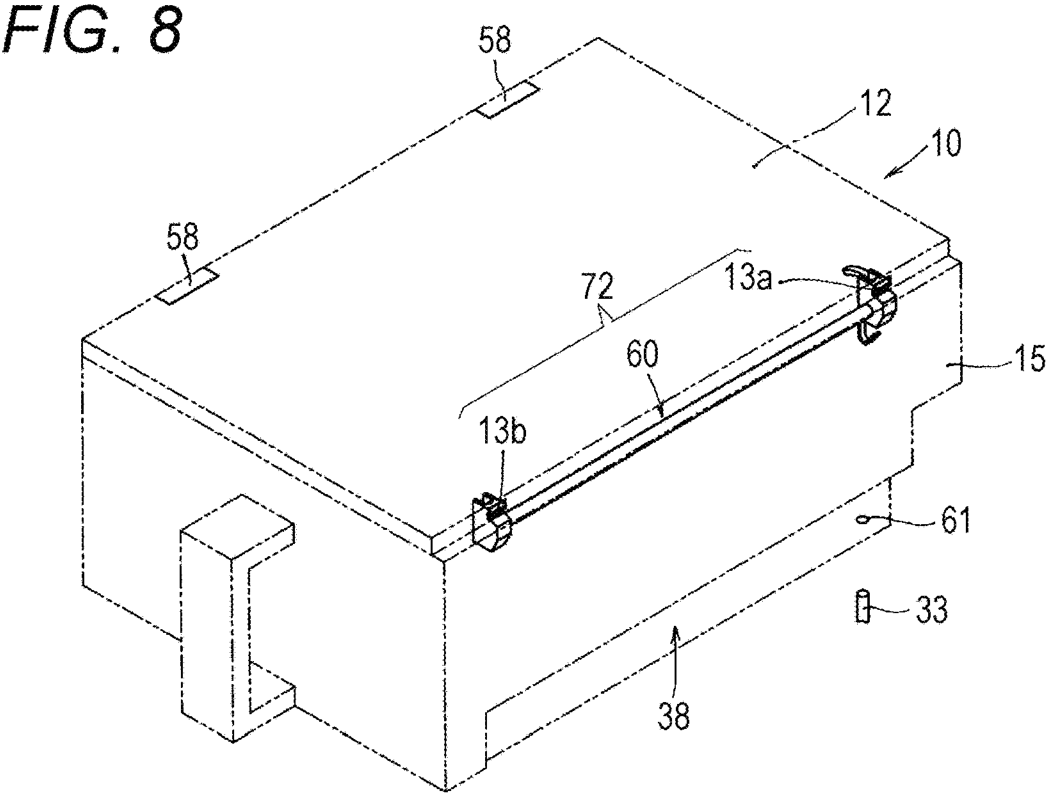
FIG. 8 is an explanatory view for conceptually illustrating lid locking means provided in the drug cassette of FIG. 2, and is an illustration of a case in which the lid locking means is in a locking state.
Figure 9:
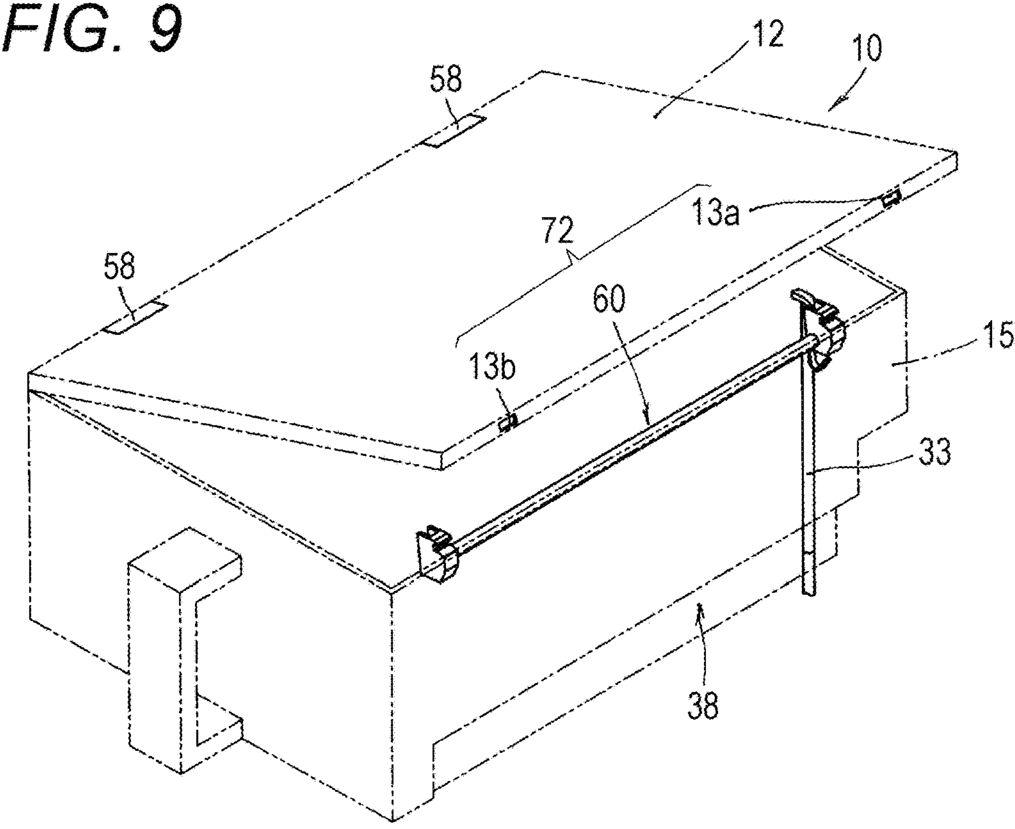
FIG. 9 is an explanatory view for conceptually illustrating the lid locking means provided in the drug cassette of FIG. 2, and is an illustration of a case in which the lid locking means is in an unlocking state.

Next, the lid member 12 of the drug cassette 10 is described with reference to FIG. 2 to FIGS. 12A and 12B. In the drug cassette 10, the lid member 12 is mounted to an upper surface of a main body 15. As illustrated in FIG. 2, FIG. 8, and FIG. 9, the lid member 12 is fixed on its one side to the main body 15 through intermediation of hinges 58. Therefore, when the lid member 12 is unlocked, the lid member 12 can be opened such that the lid member 12 is turned about the hinges 58 and a free end thereof is lifted up as illustrated in FIG. 9. The drug cassette 10 includes lid locking means 72 configured to close the lid member 12 and maintain the lid member 12 in a locked state so that the lid member 12 is prevented from being opened. In this embodiment, as illustrated in FIG. 8, FIG. 9, FIG. 11, and FIGS. 12A and 12B, the lid locking means 72 includes a lid-side first engagement portion 13*a*, a lid-side second engagement portion 13*b*, and a locking mechanism 60. The lid-side first engagement portion 13*a* and the lid-side second engagement portion 13*b* are provided to the lid member 12. The locking mechanism 60 is provided on the main body 15 side.

Figure 4:
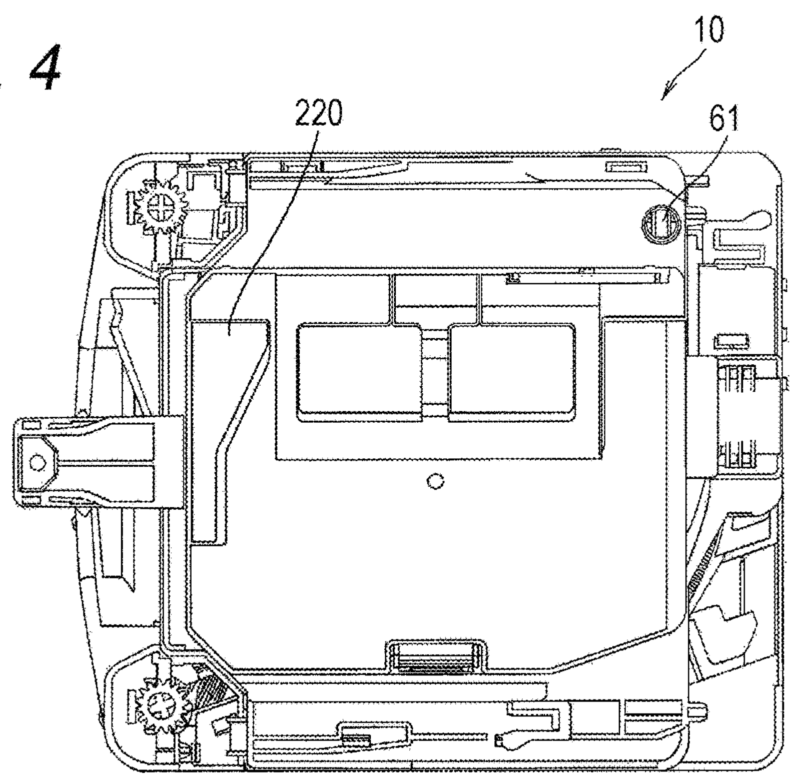
FIG. 4 is a bottom view for illustrating the drug cassette of FIG. 2.

That is, the drug cassette 10 includes the locking mechanism 60 configured to lock the lid member 12 inside the main body 15. Moreover, as illustrated in FIG. 4 and FIG. 8, a hole 61 is formed in a bottom surface of the main body 15 of the drug cassette 10. As described later, lid locking operation means 23 is provided to the cassette placement portion 8 of the drug dispensing device 1, and a rod 33 of the lid locking operation means 23 projects such that the rod 33 can be inserted through the hole 61 of the drug cassette 10. The lid locking operation means 23 unlocks the lid member 12 through operation of the locking mechanism 60 via the hole 61.

A specific configuration of the lid locking means 72 is as follows. As described above, the lid locking means 72 includes the lid-side first engagement portion 13*a* and the lid-side second engagement portion 13*b*, which are provided to the lid member 12, and the locking mechanism 60 provided on the main body 15 side. That is, in the vicinity of an end portion on the side opposite to the hinges 58 of the lid member 12, there are provided the lid-side first engagement portion 13*a* and the lid-side second engagement portion 13*b* as illustrated in FIG. 9. The lid-side first engagement portion 13*a* and the lid-side second engagement portion 13*b* are engaged with the locking mechanism 60.

Figure 10:
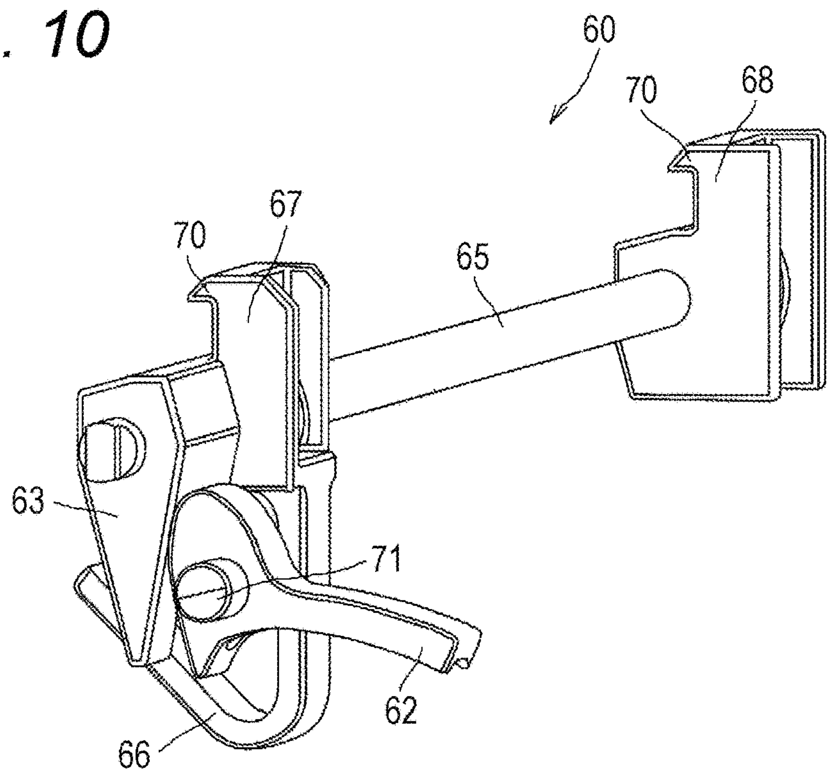
FIG. 10 is a perspective view for illustrating the lid locking means provided to the drug cassette of FIG. 2.
Figure 11:
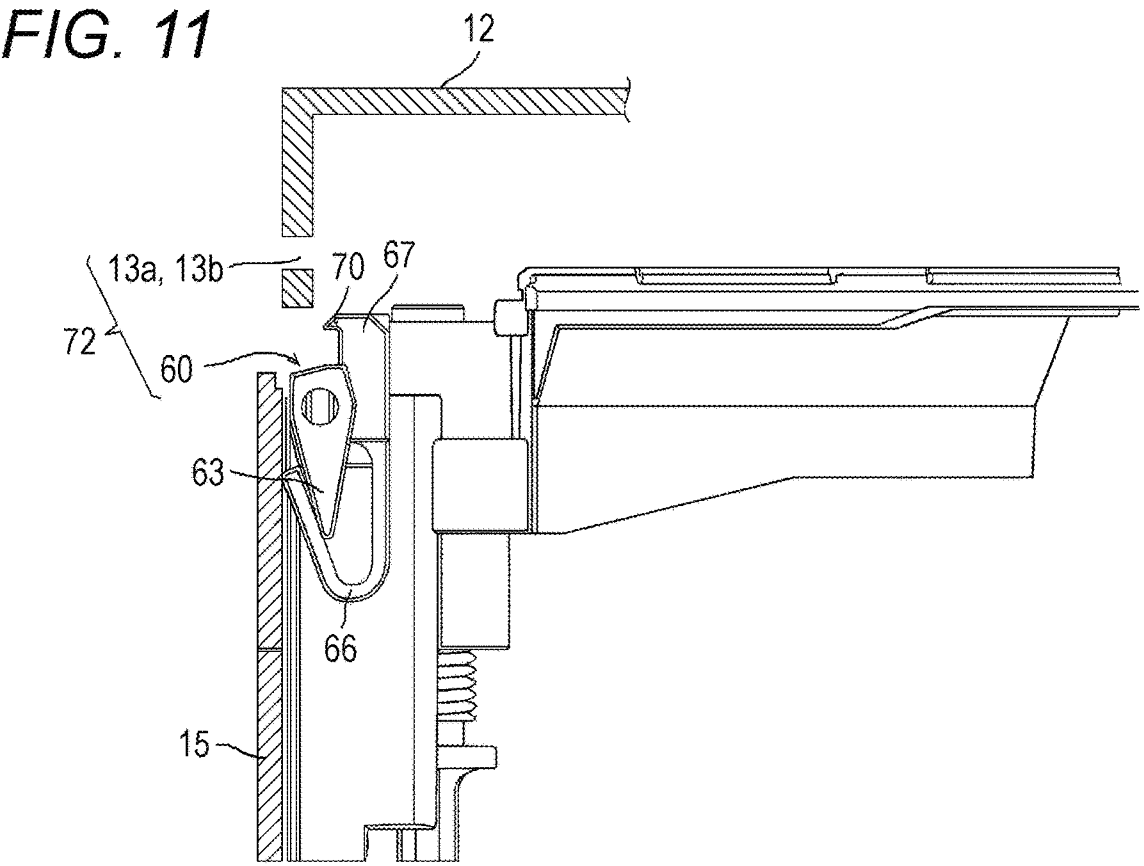
FIG. 11 is a sectional view for illustrating the surroundings of the lid locking means in the drug cassette of FIG. 2.

FIG. 10 is a perspective view for illustrating the locking mechanism 60. The locking mechanism 60 includes an operating lever 62, a power transmitting lever 63, a shaft 65, an urging member 66, a lock-side first engagement portion

67, and a lock-side second engagement portion 68. The lock-side second engagement portion 68 is mounted on one end side of the shaft 65. The power transmitting lever 63, the lock-side first engagement portion 67, and the urging member 66 are mounted on another end side of the shaft 65. The urging member 66 is formed integrally with the lock-side first engagement portion 67, and is a substantially V-shaped or U-shaped plate spring. Engagement claws 70 are formed on the lock-side first engagement portion 67 and the lock-side second engagement portion 68, respectively. The lock-side first engagement portion 67 and the lock-side second engagement portion 68 are coupled to each other by the shaft 65, and are integrally turned to be engaged with and separated from the lid-side first engagement portion 13*a* and the lid-side second engagement portion 13*b*.

Figure 12A:
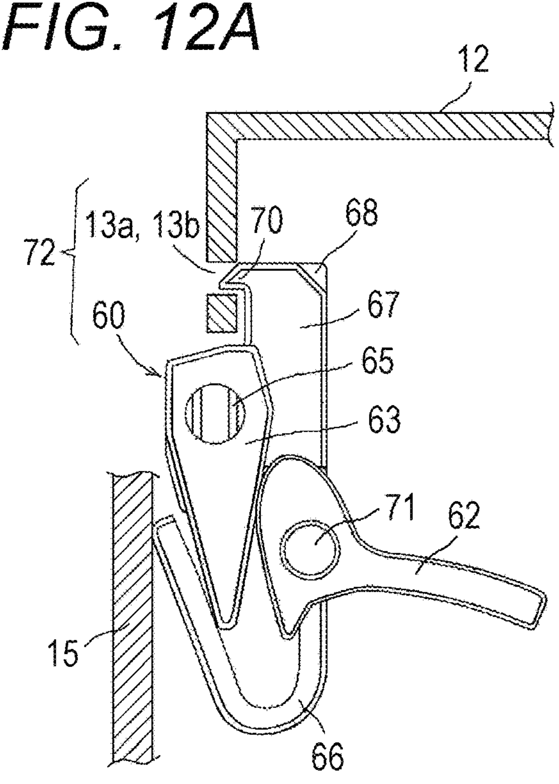
FIG. 12A is a schematic view for illustrating a state in which the lid locking means provided in the drug cassette of FIG. 2 is in a lockable state and the lid member is locked.
Figure 12B:
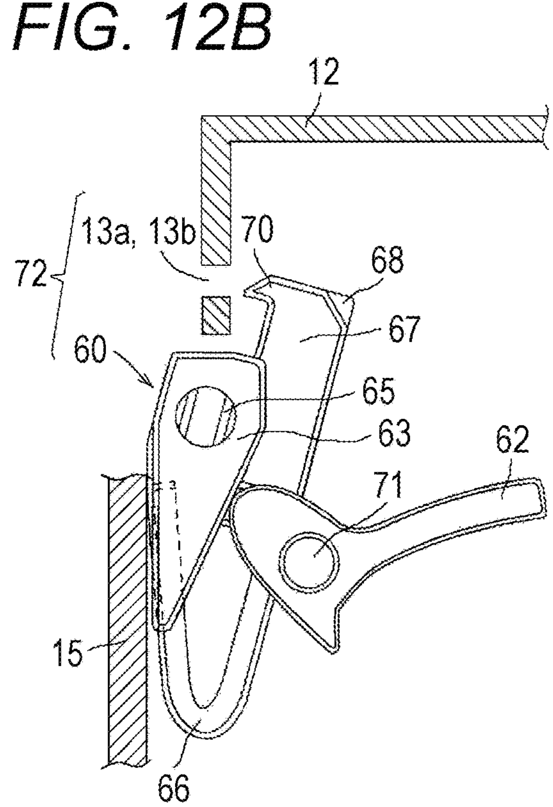
FIG. 12B is a schematic view for illustrating a state in which the lid locking means is in an unlockable state and the lid member is unlocked.

As illustrated in FIG. 8 and FIG. 9, the locking mechanism 60 is mounted on the main body 15 side of the drug cassette 10. The locking mechanism 60 is capable of assuming a posture in a lockable state and a posture in an unlocking state through swinging. FIGS. 12A and 12B are schematic views for illustrating a mechanism of locking and unlocking the lid member 12 by the locking mechanism 60. FIG. 12A is an illustration of a case in which the locking mechanism 60 is in the lockable state, and FIG. 12B is an illustration of a case in which the locking mechanism 60 is in the unlocking state. As illustrated in FIG. 12A, in a natural state (lockable state), an urging force of the urging member 66 causes the lock-side first engagement portion 67 and the lock-side second engagement portion 68 to be brought into a state of standing in a vertical posture, and the engagement claws 70 are directed in a horizontal direction. Further, in this state, the engagement claws 70 are fitted to the lid-side first engagement portion 13*a* and the lid-side second engagement portion 13*b*. Therefore, the lid member 12 is in a locked state so that an operator cannot open the lid member 12. That is, the operator cannot unlock and open the lid member 12 without use of a tool. When the locking mechanism 60 is in the lockable state, as illustrated in FIG. 12A, the operating lever 62 assumes a substantially horizontal posture.

When an external force is applied to the operating lever 62 to turn the operating lever 62 about a pin 71 as illustrated in FIG. 12B so that the operating lever 62 is inclined with its free end side located on an upper side, the first engagement portion 67 and the second engagement portion 68 assume an inclined posture so that the engagement claws 70 are pulled inward. As a result, the engagement portions 67 and 68 of the locking mechanism 60 and the engagement portions 13*a* and 13*b* on the lid member 12 side are disengaged. That is, when the operating lever 62 is turned through application of the external force, the locking mechanism 60 is brought into the unlocking state. Accordingly, the lid member 12 is brought into the unlocked state, and an operator can open the lid member 12. Meanwhile, in this embodiment, the lock-side first engagement portion 67 and the lock-side second engagement portion 68 of the locking mechanism 60 are urged by the urging member 66 in the direction of standing up. Therefore, when the external force is cancelled, the force of the urging member 66 causes the lock-side first engagement portion 67 and the lock-side second engagement portion 68 to return to the vertical posture and be brought back to the posture of being engageable with the lid member 12 side. That is, the urging member 66 causes the locking mechanism 60 to return to the lockable state. When the lid member 12 is closed in this state, the lid-side first engagement portion 13*a* and the lid-side second engagement portion 13*b* are engaged with the engagement claws 70 of the locking mechanism 60 so that the lid member 12 is brought into the locked state.

In this embodiment, the external force is applied to the operating lever 62 through use of the rod 33 of the cassette placement portion 8 to push the operating lever 62 and operate the locking mechanism 60 so that the locking mechanism 60 is brought into the unlocking state, thereby unlocking the lid member 12. Moreover, when the rod 33 separates away from the operating lever 62, the lock-side first engagement portion 67 and the lock-side second engagement portion 68 and the lid-side first engagement portion 13*a* and the lid-side second engagement portion 13*b* are brought back to the engageable posture (lockable state).

Figure 3:
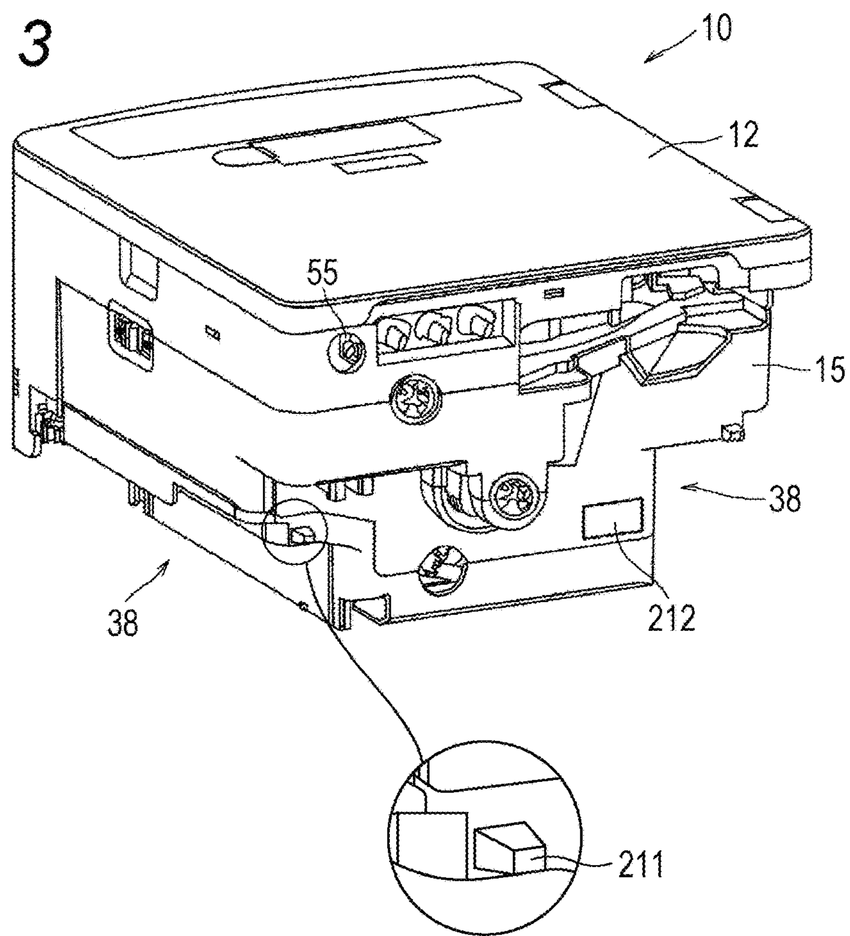
FIG. 3 is a perspective view for illustrating the drug cassette of FIG. 2 as observed from the A direction.
Figure 14:
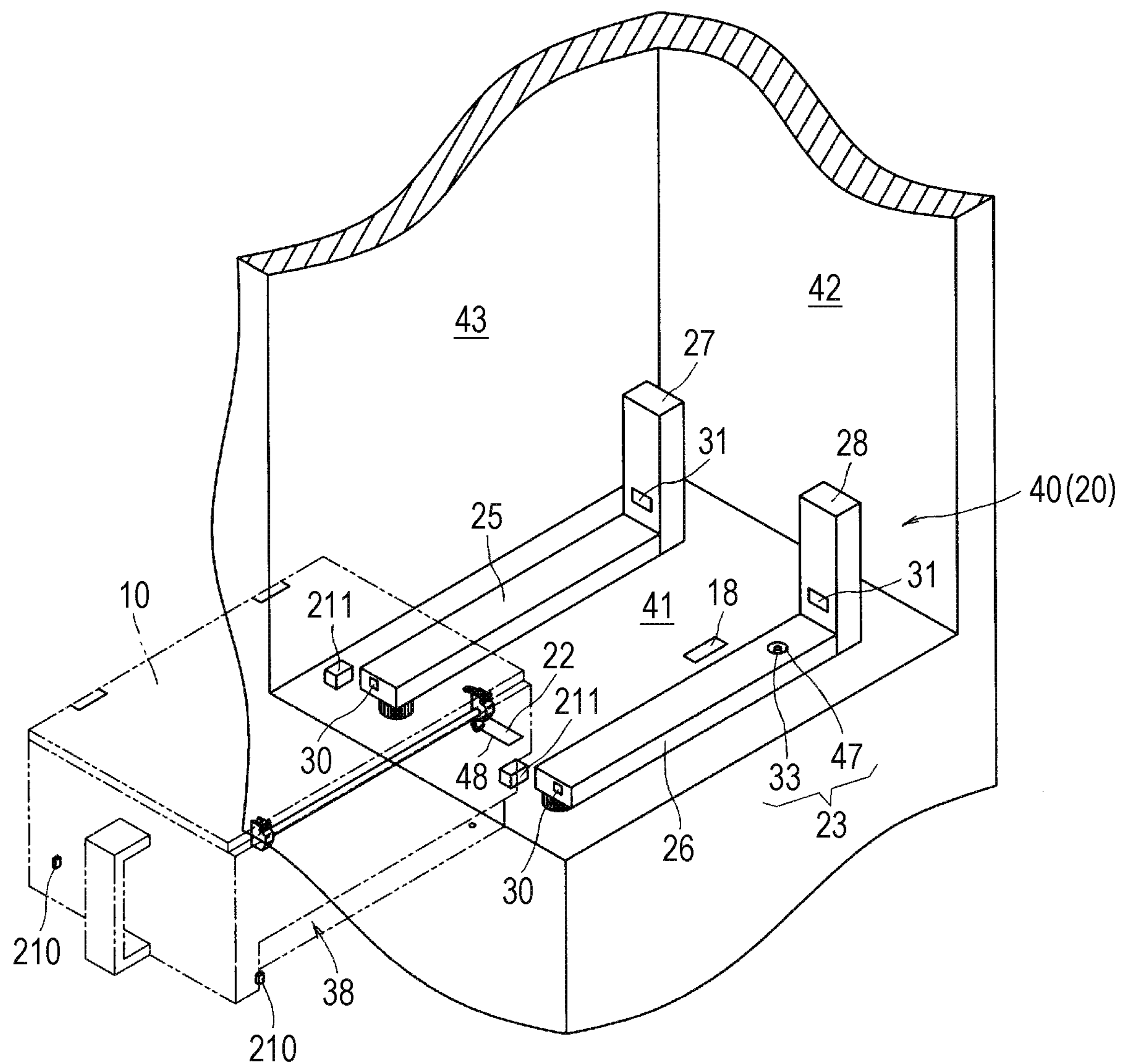
FIG. 14 is an explanatory view for illustrating a relationship between the cassette placement portion of FIG. 13 and the drug cassette at the time of mounting the drug cassette to the cassette placement portion.

Next, the contour shape of the drug cassette 10 is described. As illustrated in FIG. 2 and FIG. 3, the width of the drug cassette 10 on the lower portion side is smaller than the width on the upper portion side, and a step portion 38 is formed in the lower portion. Moreover, as illustrated in FIG. 2 and FIG. 14, small protrusions 210 are formed at a portion on a grip side in the vicinity of the step portion 38. Further, as illustrated in FIG. 3 and FIG. 14, small protrusions 211 are formed on a back side with respect to the grip in the vicinity of the step portion 38.

Now, focus is made on the bottom surface of the drug cassette 10. As illustrated in FIG. 4, the hole 61 through which the rod 33 of the lid locking operation means 23 is to be inserted is formed in the bottom surface of the drug cassette 10. The rod 33 inserted through the hole 61 reaches the operation lever 62 of the locking mechanism 60 described above. As illustrated in FIG. 4, a plurality of recess portions are formed on the back of the drug cassette 10. As one of the recess portions, there is an engagement recess portion 220 formed on the grip side. Moreover, as illustrated in FIG. 3, an RF (radio frequency) tag 212 serving as a recording medium is mounted to the drug cassette 10. This RF tag 212 is a recording medium configured to enable identification of a drug stored in the drug cassette 10. All of the drug cassettes 10 have identification information such as an identification number, and the identification information is stored in the RF tag 212.

(Cassette Placement Portion 8) Next, the cassette placement portion 8 is described with reference to FIG. 1 and FIG. 13. The cassette placement portion 8 is a portion on which the drug cassette 10 is to be temporality set (placed) to replenish the drug cassette 10 with a drug. As illustrated in FIG. 1, the cassette placement portion 8 is located at a middle-height position on the front side of the drug dispensing device 1.

In this embodiment, a recess portion 40 is formed at a corner portion on the front side of the drug dispensing device 1, forming a rack portion 20. The recess portion 40 includes a floor portion 41, a back wall portion 42, and one side wall portion 43. Further, a placement table 52, removing/locking means 22, lid locking operation means 23, and a proximity switch 18 are provided to the rack portion 20. The lid locking operation means 23 is a device configured to operate the lid locking means 72.

Figure 13:
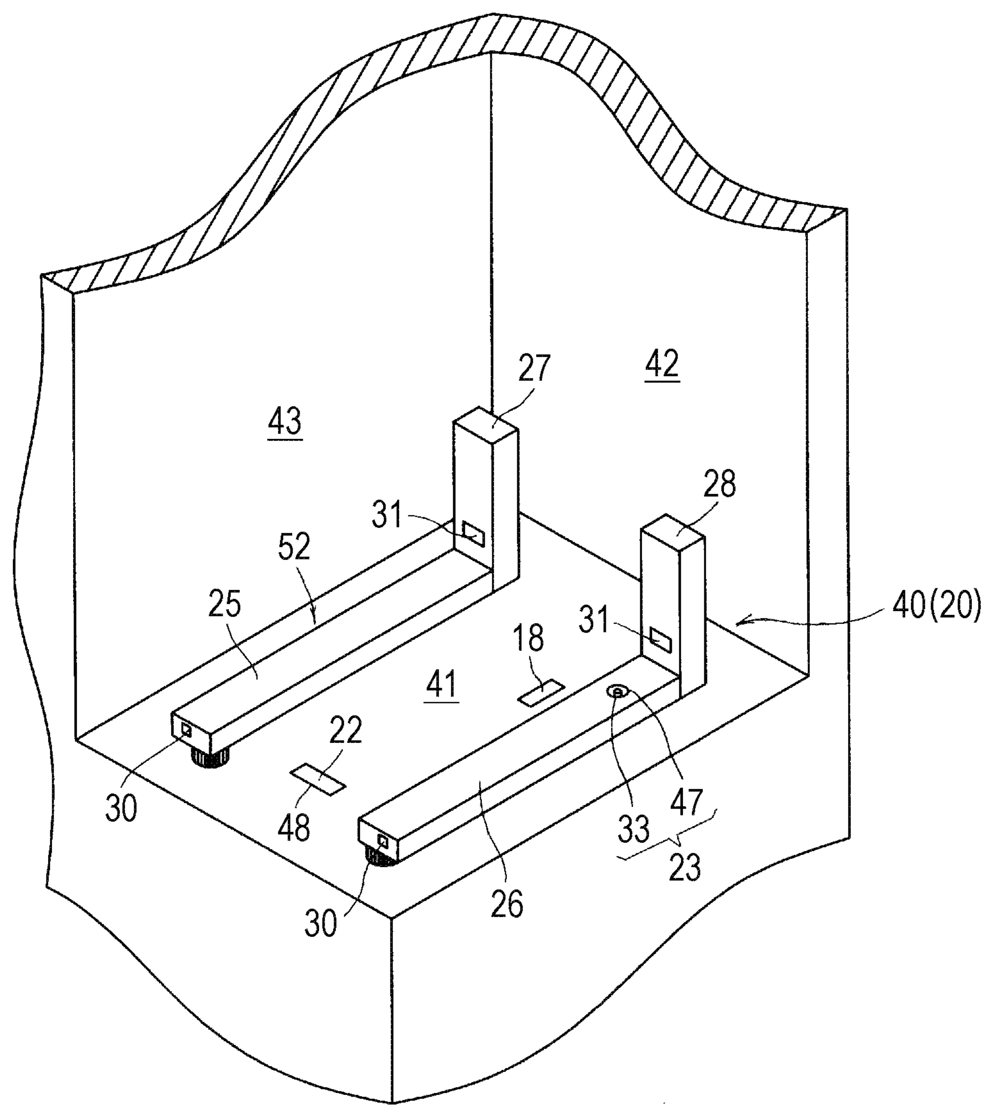
FIG. 13 is a perspective view for illustrating a cassette placement portion of the drug dispensing device of FIG. 1.

As illustrated in FIG. 13, the placement table 52 is formed of two rectangular bar members 25 and 26, which extend from the near side toward the back wall portion 42 and are arranged apart from each other in parallel. Moreover, stopper members 27 and 28 are provided in a vertical posture on the back wall portion 42 side of the rectangular bar members 25 and 26. An engagement hole 30 is formed in a projection end surface on the front side of the rectangular bar member 25. Moreover, engagement holes 31 are formed in the stopper members 27 and 28.

Figure 15:
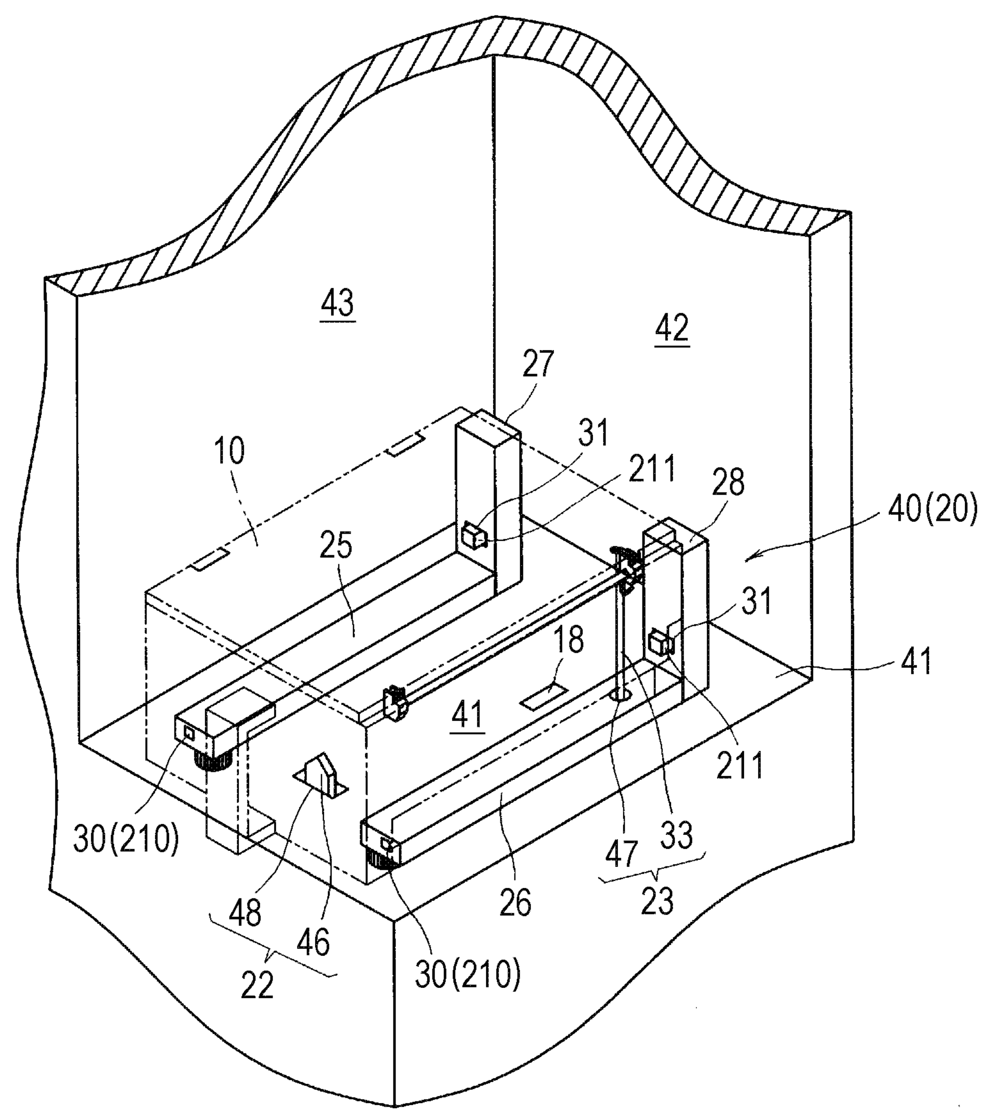
FIG. 15 is an explanatory view for illustrating a relationship between the cassette placement portion of FIG. 13 and the drug cassette in a state in which the drug cassette is mounted to the cassette placement portion.

In this embodiment, the lid locking operation means 23 is provided in the rectangular bar member 26 on one side. The lid locking operation means 23 includes the rod 33 as illustrated in FIG. 15. The rod 33 retracts in an opening 47 formed in the rectangular bar member 26 in a normal state and is caused to vertically project as needed. As a measure for causing the lid locking operation means 23 to project, there may be used the structure using a combination of a motor and a screw, a link mechanism such as a crank and a cam, or a solenoid.

The removing/locking means 22 is provided on the floor portion 41 of the rack portion 20 and is located at a position far from the back wall portion 42. Moreover, the removing/locking means 22 is located at a position between the rectangular bar members 25 and 26. The removing/locking means 22 is configured to cause an engagement piece 46 to project as illustrated in FIG. 15 from the opening 48 formed in the floor portion 41. The engagement piece 46 has a plate shape.

The proximity switch 18 is provided on the floor portion 41 of the rack portion 20, and is configured to detect that the drug cassette 10 is located at a regular position when a specified position of the drug cassette 10 arrives at the proximity switch 18.

(Operation at Time of replenishing Drug Cassette 10 with Drug) Next, a procedure for replenishing the drug cassette 10 with a drug and an operation of the drug dispensing device 1 are described. At the time of replenishing the drug cassette 10 with a drug, for the purpose of preventing erroneous replenishment of a drug or for ease of a follow-up investigation in case of any error, various checking operations are performed, and results of the checking operations are recorded. In this embodiment, input of items regarding "when", "where", "who", and "what" is made, and it is checked whether the action is appropriate. Further, the results are recorded.

In this embodiment, there is provide a computer 500 capable of communicating with the drug dispensing device 1, and predetermined information is stored in storage means (storage) 501 of the computer 500. The predetermined information may be stored in storage means (storage) provided in the drug dispensing device 1. A wide variety of information is stored in the storage means 501, but at least the following pieces of information are included. (1) Operator Information: The operator information includes information as to a pharmacist, a doctor, and a nurse who are registered to a pharmacy or a hospital, as well as a person who is permitted to operate the drug dispensing device 1, and an allowable range of operation. The operator information includes, for example, names and associated IDs of operators. (2) Drug Cassette Information: The drug cassette information includes drug-cassette identification information for identifying the drug cassette 10. Moreover, the drug cassette information includes information of a drug stored in the drug cassette 10. For example, the drug-cassette identification information and information specifying a drug name, replenishment histories, drug serial number information of a stored drug, an expiration date, and a production date are associated with each other and stored. (3) Possessed Drug Information: The possessed drug information includes information of drugs possessed by, for example, a pharmacy. Information of the drug includes a drug name, drug serial number information of the drug, an expiration date, and a production date. Moreover, a barcode affixed to a drug bottle and information of the drug are associated with each other and stored.

At the time of replenishing the drug cassette 10 with a drug, the touch-panel display (operating portion) 3 is operated to call out a predetermined drug replenishment window. The drug replenishment window has the following input columns. (1) Operation Date/Time Input Column: The operation date/time input column is a column for inputting the date and time of starting a replenishment operation. The input to the operation date/time input column may be performed through automatic input in association with a clock provided in the drug dispensing device 1, or through manual input. (2) Operator Information Input Column: A name and an ID of a person who performs the replenishment operation is to be input. When the input person is a person who is not authorized to perform replenishment of the drug, an error indication is given. (3) Drug Information Input Column: A name of a drug to be replenished is to be input. Moreover, drug serial number information of the drug, an expiration date, and a production date are input. The information including the drug serial number information, the expiration date, and the production date may be acquired from the possessed drug information and automatically input. (4) Replenishment Number Input Column: The number of a drug to be filled is to be input. The information input to the replenishment number input column can be changed later.

In this embodiment, the lid locking operation means 23 described later functions under the condition in which information of a medicine provided to a medicine bottle, information regarding a medicine accommodated in the drug cassette 10 stored in the storage means (storage) 501, and information regarding a medicine accommodated in the drug cassette 10 placed on the cassette placement portion 8 match one another, and then, as illustrated in FIG. 15, the rod 33 vertically projects from the opening 47 formed in the rectangular bar member 26. Further, the lid locking operation means described later functions under the condition in which predetermined input is given to all of the operation date/time input column, the operation information input column, the drug information input column, and the replenishment number input column after an operator replenishes the drug cassette 10 with the drug from the drug bottle, and the rod 33 is lowered and taken into the opening 47 formed in the rectangular bar member 26.

Moreover, after the replenishment operation is terminated, the input information is associated and stored in the storage means 501. That is, the items regarding "when" (information input to the operation date/time input column), "where" (specified drug dispensing device 1), "who" (information input to operator information input column), and "what" (which drug cassette 10, what drug, and how many drug") are associated and stored. At least the operator information, the date of operation, and the identification information of the drug cassette 10 are associated and stored in the storage 500. Moreover, those pieces of information are associated also with the drug serial number information or the expiration date and stored in the storage 500.

Next, an actual operation is described. In the case of replenishing the drug cassette 10 with a drug, a predetermined drug cassette 10 is removed from the container arrangement portion 200. Then, the drug cassette 10 is placed on the cassette placement portion 8. In this embodiment, the step portion 38 of the drug cassette 10 is placed on the two rectangular bar members 25 and 26 of the placement table 52, and then, in that state, the drug cassette 10 is pushed in toward the back wall portion 42 side.

A distal end portion of the drug cassette 10 is brought into abutment against the stopper members 27 and 28 and cannot be further pushed in. Moreover, the small protrusions 211 of the drug cassette 10 are brought into engagement with the engagement holes 31 formed in the stopper members 27 and 28. Further, the small protrusions 210 of the drug cassette 10 are brought into engagement with the engagement hole 30 formed on the front side of the rectangular bar member 25.

As a result, the drug cassette 10 is positioned at a specified position on the cassette placement portion 8. That is, the drug cassette 10 is positioned in the insertion direction of the drug cassette 10 through the abutment of the distal end portion of the drug cassette 10 against the stopper members 27 and 28. The drug cassette 10 is positioned in the right-and-left direction of the drug cassette 10 though the engagement of the step portion 38 of the drug cassette 10 with the two rectangular bar members 25 and 26 of the placement table 52 and further through the engagement of the small protrusions 210 and 211 of the drug cassette 10 with the engagement holes 30 and 31. Further, upward movement of the drug cassette 10 is regulated through the engagement of the small protrusions 210 and 211 of the drug cassette 10 with the engagement holes 30 and 31.

The proximity switch 18 is provided on the floor portion 41 of the rack portion 20. When it is confirmed through use of the proximity switch 18 that the drug cassette 10 is located at the specified position, the removing/locking means 22 operates automatically or based on a predetermined operation so that the plate-shaped engagement piece 46 projects from the opening 48 formed in the floor portion 41 as illustrated in FIG. 15. Then, the engagement piece 46 is engaged with the engagement recess portion 220 formed on the back of the drug cassette 10. As a result, the drug cassette 10 is brought into a state in which the drug cassette 10 cannot be removed from the cassette placement portion 8. Further, the drug cassette 10 is brought into a state in which a position of the drug cassette 10 cannot be changed on the cassette placement portion 8. In this state, the position of the hole 61 formed in the bottom of the drug cassette 10 matches with the position of the opening 47 from which the rod 33 provided to the rectangular bar member 26 protrudes. Moreover, identification information of the drug cassette 10 is read from the RF tag 212 provided to the drug cassette 10, and determination is made on whether or not the drug cassette 10 is the drug cassette 10 to be replenished with the drug.

Then, the operator takes a drug bottle (not shown), which stores the drug desired to be replenished by the operator, from, for example, a medicine storage or a medicine rack. Typically, a symbol such as a barcode or a two-dimensional code is printed on a label of a drug bottle storing a drug. This symbol includes information relating to the drug stored in the bottle. The operator uses the optical scanner 5 to read the symbol provided to the bottle. Based on a result of the scanning, the drug dispensing device 1 specifies the drug contained in the drug bottle.

Next, the drug dispensing device 1 determines whether or not the drug contained in the drug bottle is a correct drug to be replenished into the drug cassette 10. When the drug contained in the drug bottle is an incorrect drug to be replenished into the drug cassette 10, a predetermined warning is displayed. When the drug contained in the drug bottle is a correct drug to be replenished into the drug cassette 10, the lid locking operation means 23 functions automatically or based on a predetermined operation, and the rod 33 vertically projects from the opening 47 formed in the rectangular bar member 26 as illustrated in FIG. 15.

As described above, the position of the opening 47 formed in the rectangular bar member 26 matches with the hole 61 formed in the bottom of the drug cassette 10. Thus, the rod 33 projecting from the opening 47 is inserted through the hole 61 of the drug cassette 10 and collides with the operating lever 62, thereby applying an upward external force to the operating lever 62. As a result, the lock-side first engagement portion 67 and the lock-side second engagement portion 68 of the locking mechanism 60 assume the inclined posture so that the engagement claws 70 are pulled inward, thereby cancelling the engagement with the lid-side first engagement portion 13*a* and the lid-side second engagement portion 13*b*. That is, the rod 33 changes the posture of the locking mechanism 60 from the lockable state to the unlocking state. As a result, the unlocked state of the lid member 12 is brought about.

After that, the operator opens the lid member 12 by hand, and the drug is replenished into the solid-preparation receiving portion 11 inside. After the replenishment of the drug is terminated, the operator closes the lid member 12 by hand. Then, the operator operates the touch-panel display (operating portion) 3 to input the information that the drug has been charged into the drug cassette 10. The operator checks, for example, the amount of the replenished drug even after closing the lid member 12.

Then, when the operator is confident that there is no mistake, the operator operates the touch-panel display (operating portion) 3 to bring the locking mechanism 60 of the drug cassette 10 from the unlocking state into a locking state. Specifically, when a confirming portion of the touch-panel display 3 is operated based on the operator's intention, the lid locking operation means 23 functions so that the rod 33 is lowered and taken into the opening 47 formed in the rectangular bar member 26. As a result, the operating lever 62 of the locking mechanism 60 loses the external force, and the urging member 66 causes the lock-side first engagement portion 67 and the lock-side second engagement portion 68 to return to the vertical posture and be brought back into the posture of being engageable with the lid member 12. That is, the rod 33 causes the locking mechanism 60 to change the posture from the unlocking state to the lockable state. As described above, the lid member 12 is closed by the operator, and hence the engagement claws 70 of the locking mechanism 60 are engaged with the lid-side first engagement portion 13*a* and the lid-side second engagement portion 13*b* of the lid member 12 so that the lid member 12 is brought into the locked state.

Further, the removing/locking means 22 operates so that the projecting engagement piece 46 is taken into the opening 48 formed in the floor portion 41. As a result, the engagement piece 46 and the engagement recess portion 220 formed on the back of the drug cassette 10 are disengaged. Any one of the disengagement by the removing/locking means 22 and the operation of the operating lever 62 of the locking mechanism 60 by the lid locking operation means 23 may come first. That is, the disengagement by the removing/locking means 22 may be performed after the lid locking means 72 is brought into the lockable state by the lid locking operation means 23, or the lid locking means 72 may be brought into the lockable state by the lid locking operation means after the disengagement by the removing/locking means 22 is performed. That is, when the condition that the lid locking means 72 is brought into the lockable state by the lid locking operation means 23 is met, the removing/locking means 22 may be cancelled so that the drug cassette 10 is removable from the cassette placement portion 8. Moreover, with the condition that, after the lid locking operation means 23 functions, the operator further operates the touch-panel display 3, the removing/locking means 22 may be cancelled so that the drug cassette 10 is removable from the cassette placement portion 8.

In this embodiment, even after the lid member 12 is once closed, unless the confirming portion of the touch-panel display 3 is operated based on the operator's intention so that the lid locking operation means 23 functions, the lid member 12 can be re-opened. That is, in this embodiment, unless the lid locking operation means 23 is allowed to function based on the operator's intention, the rod 33 of the lid locking operation means 23 maintains the projecting state and continues pressing the operating lever 62 of the locking mechanism 60. Therefore, the lid member 12 is closed in appearance but is not in the locked state. Accordingly, the lid member 12 can be re-opened by the operator's hand. For example, when the operator feels that the drug is not sufficient, the operator can re-open the lid member 12 and add the drug. In contrast, when the operator feels that the drug is excessive, the operator can re-open the lid member 12 and scoop up the drug with a spoon or the like to reduce the drug.

In this embodiment, the cassette placement portion 8 is provided at a part of the main body portion of the drug dispensing device 1. However, this disclosure is not limited to this configuration, and the cassette placement portion 8 may be provided separately from the main body portion of the drug dispensing device 1. In this embodiment, as means for expressing the intention to bring the lid member 12 into the locked state, the touch-panel display 3 is exemplified. However, this disclosure is not limited to this configuration. There may be provided a switch or the like (operating portion) for confirming completion of the replenishment or a switch or the like (operating portion) for suggesting the same, and those switches may be operated by an operator.

In the embodiment described above, the locking mechanism 60 serving as a drive portion for the lid locking means 72 is provided to the main body 15 of the drug cassette 10, and the engagement portions to be engaged with the locking mechanism 60 are provided to the lid member 12. This disclosure is not limited to this configuration. Members to be driven by the rod 33 and other components may be provided on the lid member 12 side, and members to be engaged therewith may be provided to the main body 15.

The locking mechanism 60 configured to lock the lid member 12 of the drug cassette 10 is not limited to the configuration of the embodiment described above, and may be the one using a toggle mechanism, the one using a screw or a bolt, or the one using electromagnetic means. The locking mechanism 60 is only required to be capable of locking such that the lid member 12 cannot be opened without a tool or equipment.

Similarly, the lid locking operation means is not limited to the configuration in which the rod 33 vertically moves. For example, the lid locking operation means may have a configuration in which the rod 33 or another action piece horizontally moves or swings. Moreover, the lid locking operation means may have a configuration in which the action piece rotates or may be the one using electromagnetic means. Moreover, the lid locking operation means may have a configuration in which the locking mechanism is operated in a non-contact manner.

In the embodiment described above, unless the lid locking operation means 23 functions based on the operator's intention, the locking mechanism 60 maintains the unlocking state and is not engaged with the lid-side first engagement portion 13*a* and the lid-side second engagement portion 13*b*. That is, in this embodiment, unless the lid locking operation means 23 functions based on the operator's intention, the free end side of the lid member 12 is not engaged with any member so that the lid member 12 is in a free state. This disclosure is not limited to this configuration, and the locking mechanism 60 may be brought into a state of being semi-engaged with the lid member 12. For example, when the locking mechanism 60 is in the state of being semi-engaged with the lid member 12, the lid member 12 is in a state of being closed. However, when the lid member 12 is opened with a strong force, the engagement is cancelled, and the lid member 12 is opened. Moreover, there may be used a configuration in which, unless the lid locking operation means 23 functions based on the operator's intention, the locking mechanism 60 is in a temporal locking state so that the state in which the lid member 12 is closed can be maintained through a simple manual operation.

The drug cassette 10 of this embodiment includes the inner rotary body and the outer rotary body. However, this configuration is merely one example of the drug cassette 10. There may be provided only one rotary body, or the rotary body may be omitted in the first place.

Figure 16:
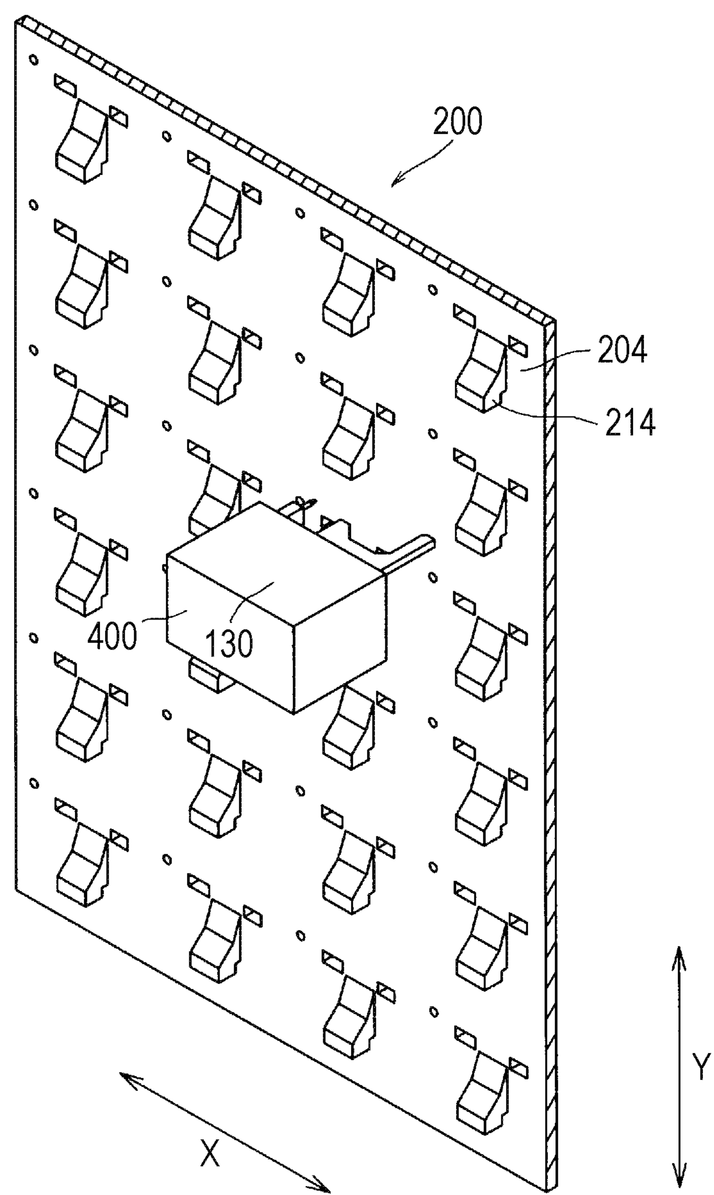
FIG. 16 is a sectional view for illustrating an inside of the drug dispensing device illustrated in FIG. 1, as observed from a back side of a container arrangement portion.

(Vial Conveying Device 130) The vial conveying device 130 is installed inside the drug dispensing device 1. As illustrated in FIG. 16, the vial conveying device 130 is provided on the back side of the container arrangement portion 200 and includes a moving head 400. The moving head 400 is configured to move in a longitudinal direction (X direction) of the drug dispensing device 1 on the back side of the container arrangement portion 200 along a rail (not shown). Moreover, the moving head 400 is held by a raising/lowering device (not shown) and is configured to move also in an up-and-down direction (Y direction). That is, the moving head 400 is held on an X-Y table of a kind and is configured to move planarly on the back side of the container arrangement portion 200. Moreover, the moving head 400 is configured to move in directions of approaching and separating from the back of the container arrangement portion 200.

Figure 17:
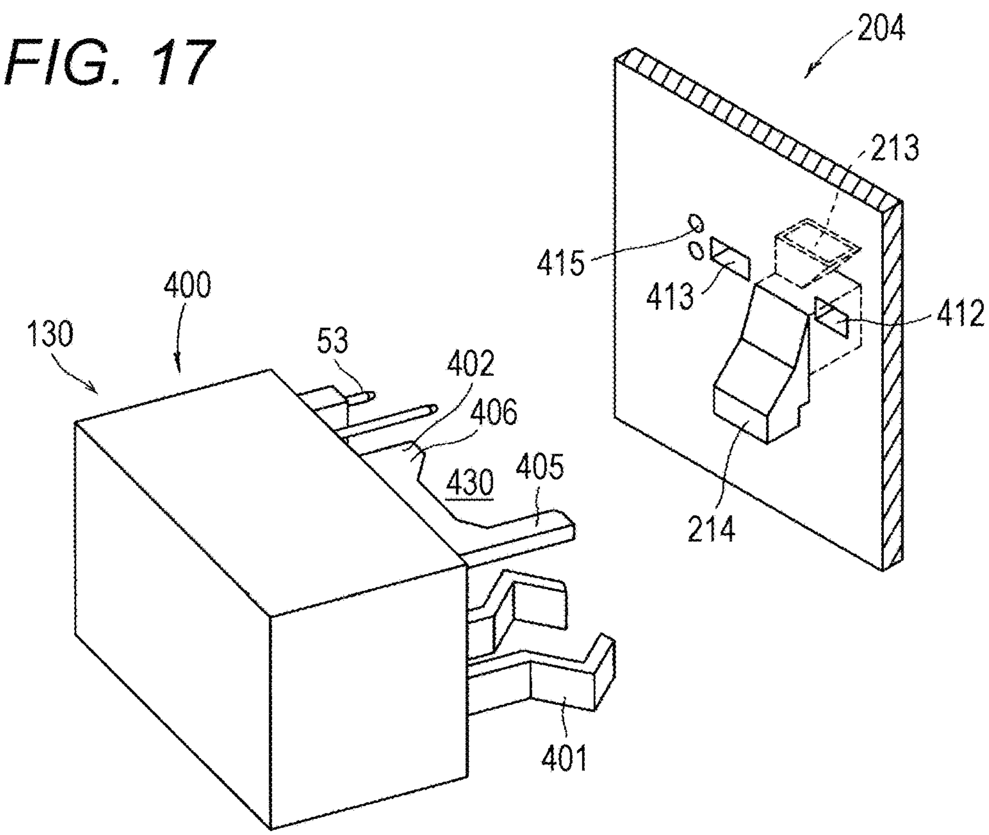
FIG. 17 is a configuration view for illustrating a part of the container arrangement portion on the back side and a moving head.
Figure 18:
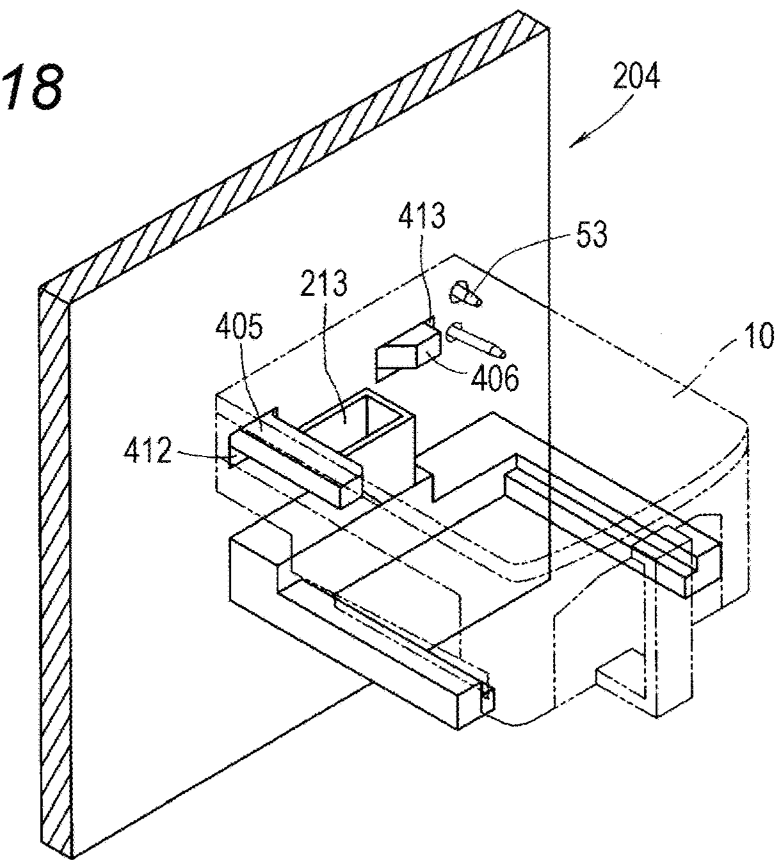
FIG. 18 is a partial enlarged view for illustrating an exterior side of the drug dispensing device illustrated in FIG. 1, and is an illustration of a drug-cassette mounting portion of the container arrangement portion.
Figure 19A:
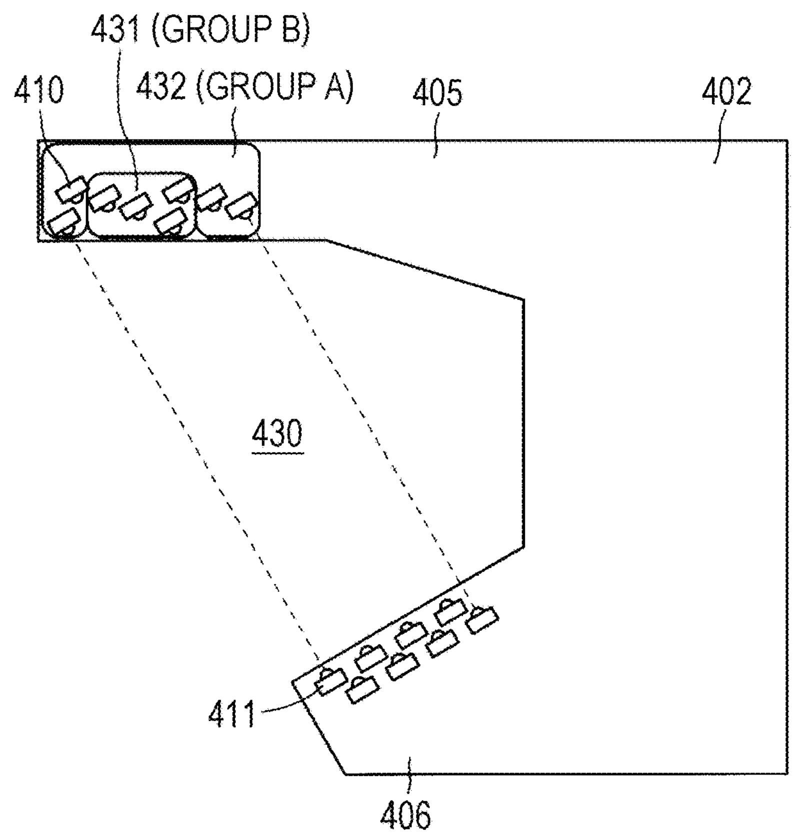
FIGS. 19A and 19B are each a configuration view for illustrating an arrangement of light-emitting members and light-receiving members of drug counting means.
Figure 19B:
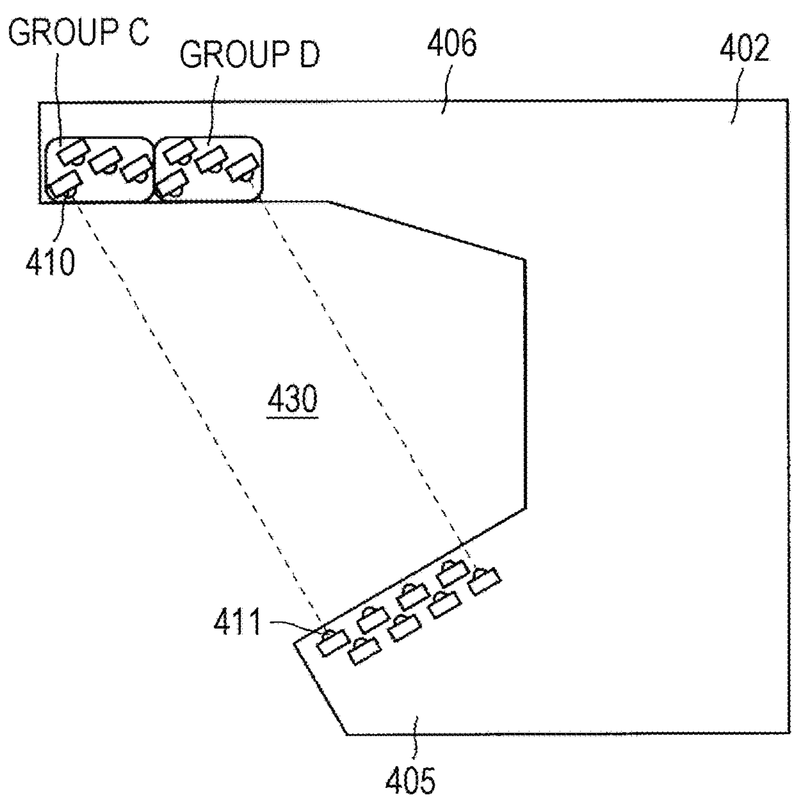

As illustrated in FIG. 17, a chuck 401 configured to hold a vial, a drug counting board (drug counting means) 402, and an overflow sensor 53 (drug detection sensor) are provided to the moving head 400. The drug counting board 402 includes two arm members 405 and 406 as illustrated in FIG. 17 and FIGS. 19A and 19B, and is configured to count, through use of an optical sensor, the number of tablets which pass through a space between the arm members 405 and 406. One arm member 405 is a light-emitting-side arm in which a plurality of light-emitting elements 410 are arranged as illustrated in FIG. 19A.

Another arm member 406 is a light-receiving-side arm in which a plurality of light-receiving elements 411 are arranged as illustrated in FIG. 19A. The plurality of light-emitting elements 410 and the plurality of light-receiving elements 411 are provided to the two arm members 405 and 406 which are located at positions apart from each other, and a predetermined distance is given therebetween. The drug counting board 402 detects that, when tablets pass through a planar space 430 surrounded by the light-emitting elements 410 and the light-receiving elements 411 and block light emitted from the light-emitting elements 410, reception of the light by the light-receiving elements 411 is interrupted, and then counts the amount of the drug having passed through the planar space 430.

In this embodiment, eight light-emitting elements (light-emitting members) 410 are mounted to the light-emitting-side arm member 405. Moreover, eight light-receiving elements (light-receiving members) 411 are mounted to the light-receiving-side arm member 406. In this embodiment, the eight light-emitting elements 410 are grouped into two light-emitting-element groups 431 and 432 surrounded by frames. Among the eight light-emitting elements 410, four light-emitting elements 410 in total, specifically, two light-emitting elements 410 located closer to the open end side of the light-emitting-side arm member 405 and two light-emitting elements 410 located closer to the base end side of the light-emitting side arm member 405 form a group A. Moreover, four light-emitting elements 410 located closer to the center form a group B.

In this embodiment, the light emission quantity is controlled for each group. That is, the four light-emitting elements 410 belonging to the group A emit light with the same light emission quantity. Moreover, the four light-emitting elements 410 belonging to the group B emit light with the same light emission quantity. Moreover, the light-emitting elements 410 may be grouped, for example, as illustrated in FIG. 19B. The number of light-emitting elements 410 and the number of groups are freely selected, and it is preferred that the numbers be larger.

As illustrated in FIG. 16, on the back side of the container arrangement portion 200, there are provided a plurality of drug dispensing ports 214 arranged in such a manner as to correspond to the drug-cassette mounting portions 204 of the container arrangement portion 200. Moreover, the drug-cassette mounting portions 204 of the container arrangement portion 200 have drug charging ports 213 communicating with the drug dispensing ports 214 described above. The drug cassette 10 is set to the drug-cassette mounting portion 204 on the front side, and tablets are delivered from the drug cassette 10 to the drug dispensing port 214.

In a wall surface of the container arrangement portion 200, there are formed openings 412 and 413 and sensor insertion ports 415 passing through the front and back of the wall. The arm members 405 and 406 of the drug counting board 402 described above are inserted into the openings 412 and 413 from the back side of the container arrangement portion 200, and the arm members 405 and 406 can pass through the openings 412 and 413 and project toward the front side of the container arrangement portion 200. Moreover, the sensor insertion ports 415 are formed in such a manner that an optical axis of light radiated by the overflow sensor 53 passes therethrough.

That is, the moving head 400 is movable in the direction of approaching and separating away from the back of the container arrangement portion 200 so that the arm members 405 and 406 can be caused to project from the openings 412 and 413 toward the front side by moving the moving head 400 toward the wall surface side of the container arrangement portion 200. Then, the two arm members 405 and 406 project to the position of covering the drug charging port 213, and the drug delivered from the drug cassette 10 passes through the planar space 430 surrounded by the two arm members 405 and 406 at the time of falling into the drug charging port 213, and then is counted.

(Function of Overflow Sensor 53) In the drug cassette 10 of this embodiment, the dispensing passage 35 is formed of the second rotary body 51 as described above. The overflow sensor 53 (drug detection sensor) is a sensor configured to detect whether or not tablets are present on the dispensing passage 35. As described above, the overflow sensor 53 emits light through the hole 73 facing the dispensing passage 35 formed of the second rotary body 51 and receives light reflected from the tablets at a light-receiving portion, thereby detecting the presence or absence of the tablets. Here, in this embodiment, in addition to the determination of the presence or absence of the tablets based on an absolute value of the reflected light, the presence or absence of the solid drug is determined based also on the amount of change in the reflected light per unit time.

That is, some tablets are less likely to reflect light. When the determination relies only on the intensity of reflected light, in some cases, it is determined that tablets are not present even through tablets are present on the second rotary body 51. As a result, the first rotary body 50 rises so that the height of an upper portion of a group of tablets reaches a height of the second rotary body 51 provided on the outer side. Therefore, there is a fear in that, even though the tablets have moved from the first rotary body 50 onto the second rotary body 51 so that the timing for stopping the rise of the first rotary body 50 has come, the first rotary body 50 continues rising, with the result that the tablets overflow onto the dispensing passage 35. In view of such problem, in this embodiment, for the purpose of more reliably determining the presence of the drug on the second rotary body 51, in addition to the determination of the presence or absence of tablets based on the absolute value of the reflected light, the determination on whether or not the solid drug is present is performed based also on the amount of change in the reflected light per unit time. That is, the determination on whether or not the solid drug is present is performed based also on a differential value of the reflected light.

When tablets which are less likely to reflect light have moved onto the second rotary body 51, due to the weakness in reflected light, the intensity of the light received by the light-receiving portion does not reach a threshold for the determination of the presence of the tablets in some cases. However, the tablets move or change the posture on the second rotary body 51, and hence the reflected light may flicker. Therefore, even when, though the intensity of the received light does not reach the threshold for the determination of the presence of the tablets, the received light may flicker to an extent of exceeding the normal level, and the amount of change per unit time reaches a certain threshold, it is determined that the tablets have moved onto the second rotary body 51. As a matter of course, when the amount of change (differential value) per unit time does not reach the certain threshold, and the absolute value of the reflected light exceeds the threshold, it is determined that the tablets are present on the second rotary body 51.

In the drug dispensing device 1 according to this embodiment, the first rotary body 50 provided on the inner side slowly rises while rotating at the time of dispensing the drug, thereby causing the tablet group placed on the first rotary body 50 to rise while rotating the tablet group. When the quantity of light received by the overflow sensor 53 exceeds the threshold, or the amount of change per unit time reaches the threshold, the rise of the first rotary body 50 is stopped, and the first rotary body 50 rotates at that height and supplies the tablets to the second rotary body 51 provided on the outer side. The second rotary body 51 provided on the outer side rotates so that the tablets on the second rotary body 51 are conveyed toward the tablet delivery port 17.

The drug cassette 10 used in this embodiment includes the solid-preparation receiving portion 11 configured to receive a solid drug, a delivery port (tablet delivery port 17) configured to deliver the solid drug from the solid-preparation receiving portion 11, and the rotary body 51, and is configured to place the solid drug on the rotary body 51 and rotate the rotary body 51 to move the solid drug to the delivery port 17. The drug cassette 10 includes the overflow sensor 53 configured to detect whether or not the solid drug is present on the rotary body 51. The overflow sensor 53 includes the light-emitting portion and the light-receiving portion, and is configured to receive the light reflected from the solid drug at the light-receiving portion, thereby determining whether or not the solid drug is present based on the amount of change in the reflected light per unit time.

Figure 20:
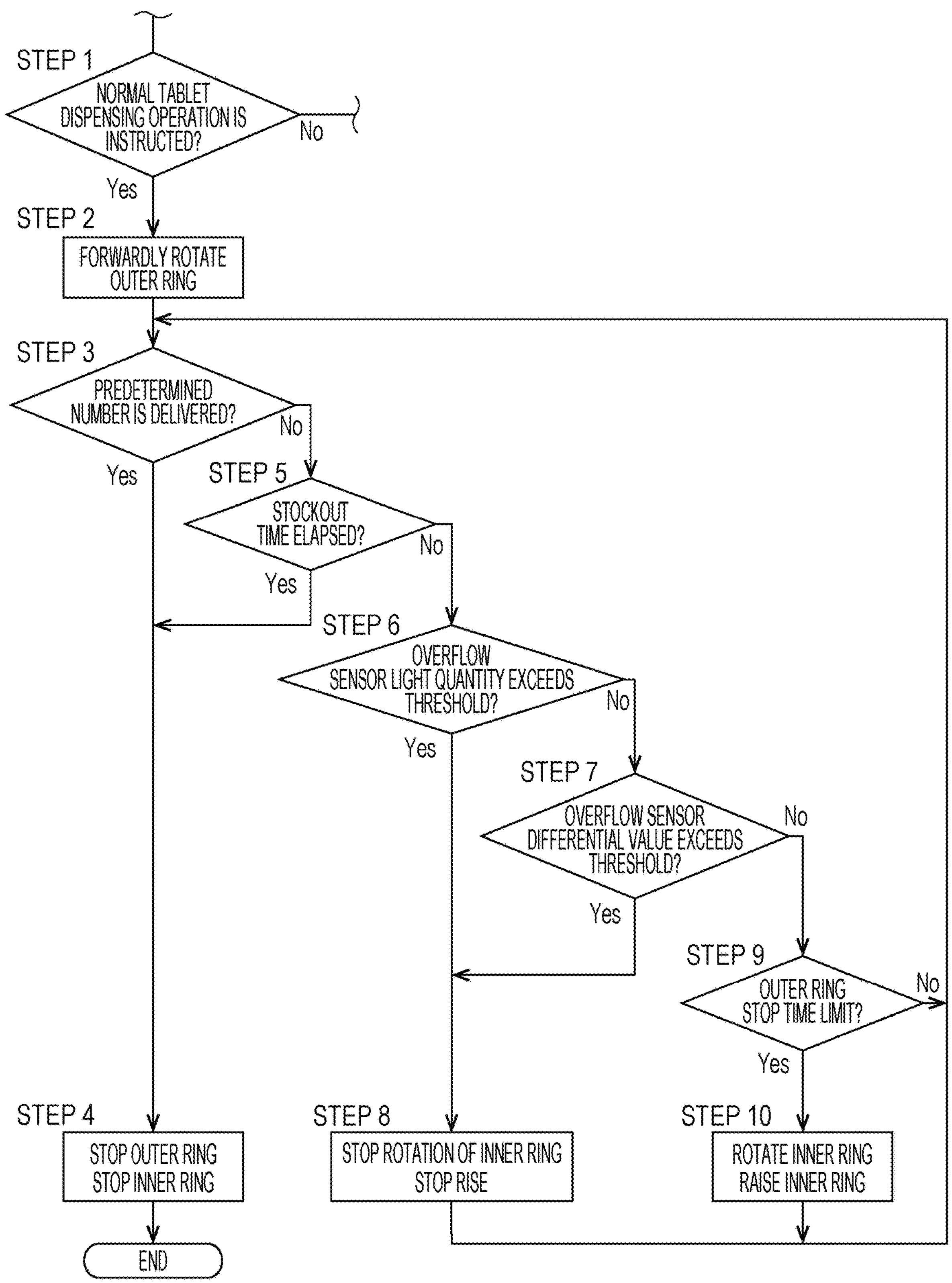
FIG. 20 is a flowchart for illustrating a part of the operation of the drug dispensing device, and is an illustration of an operation of dispensing a tablet from the drug cassette through a normal dispensing operation.

In this embodiment, the detection of the tablets on the second rotary body 51 is performed based on the absolute value of the reflected light and the amount of change (differential value) per unit time. Thus, in the drug dispensing device 1 according to this embodiment, an operation to be performed at the time of dispensing tablets from the drug cassette 10 through normal dispensing operation is as illustrated in a flowchart of FIG. 20.

When the normal dispensing operation is selected in Step 1, the operation proceeds to Step 2, and the second rotary body (outer ring) 51 starts forward rotation. Next, the operation proceeds to Step 3, determination is made on whether or not a predetermined amount of tablets have been delivered. When a predetermined amount of tablets have been delivered, the operation proceeds to Step 4, and the operation of the drug cassette 10 is stopped, thereby terminating the series of operation.

Meanwhile, when a predetermined amount of tablets have not been delivered yet, the operation proceeds to Step 5, and determination is made on whether or not a stockout detection time has elapsed. That is, in a case in which the drug is not delivered even after the second rotary body 51 is rotated for a certain time period, it is determined that the drug cassette 10 is empty. Then, the operation proceeds to Step 4, and the operation of the drug cassette 10 is stopped, thereby terminating the series of operations.

When the stockout detection time has not elapsed, the operation proceeds from Step 5 to Step 6 and further to Step 7, and determination is made on whether or not the quantity of light exceeds the threshold of the absolute value of the quantity of light received by the overflow sensor 53 or whether or not the quantity of light exceeds the threshold of the differential value. When the quantity of light exceeds any one of the thresholds, the operation proceeds to Step 8, and the rise of the first rotary body (inner ring) 50 is stopped. Then, the operation returns to Step 3. When the first rotary body (inner ring) 50 has not started rotating and rising, this state is maintained, and the operation returns to Step 3. When it is determined that the quantity of light has not exceeded any one of the thresholds in Step 6 and Step 7, the operation proceeds to Step 9, and determination is made on whether or not a certain outer-ring drive time limit has been reached. When the outer-ring drive time limit has not been reached, it is expected that the tablet group has not risen to the second rotary body. Thus, the operation proceeds to Step 10, and the inner ring is rotated and raised. Then, the operation returns to Step 3.

Moreover, in this embodiment, as an operation of dispensing a drug from the drug cassette 10, a timer-control dispensing operation can be performed. The timer-control dispensing operation is a method of raising the first rotary body 50 for only a certain time period and then stopping the rise for a certain time period. At the time of performing the timer-control dispensing operation, the drug may be detected based on both of the absolute value of the reflected light and the amount (differential value) of change per unit time. However, only the differential value may be used for the timer-control dispensing operation because it is difficult to detect the drug based on the absolute value of the reflected light in many cases.

Figure 21:
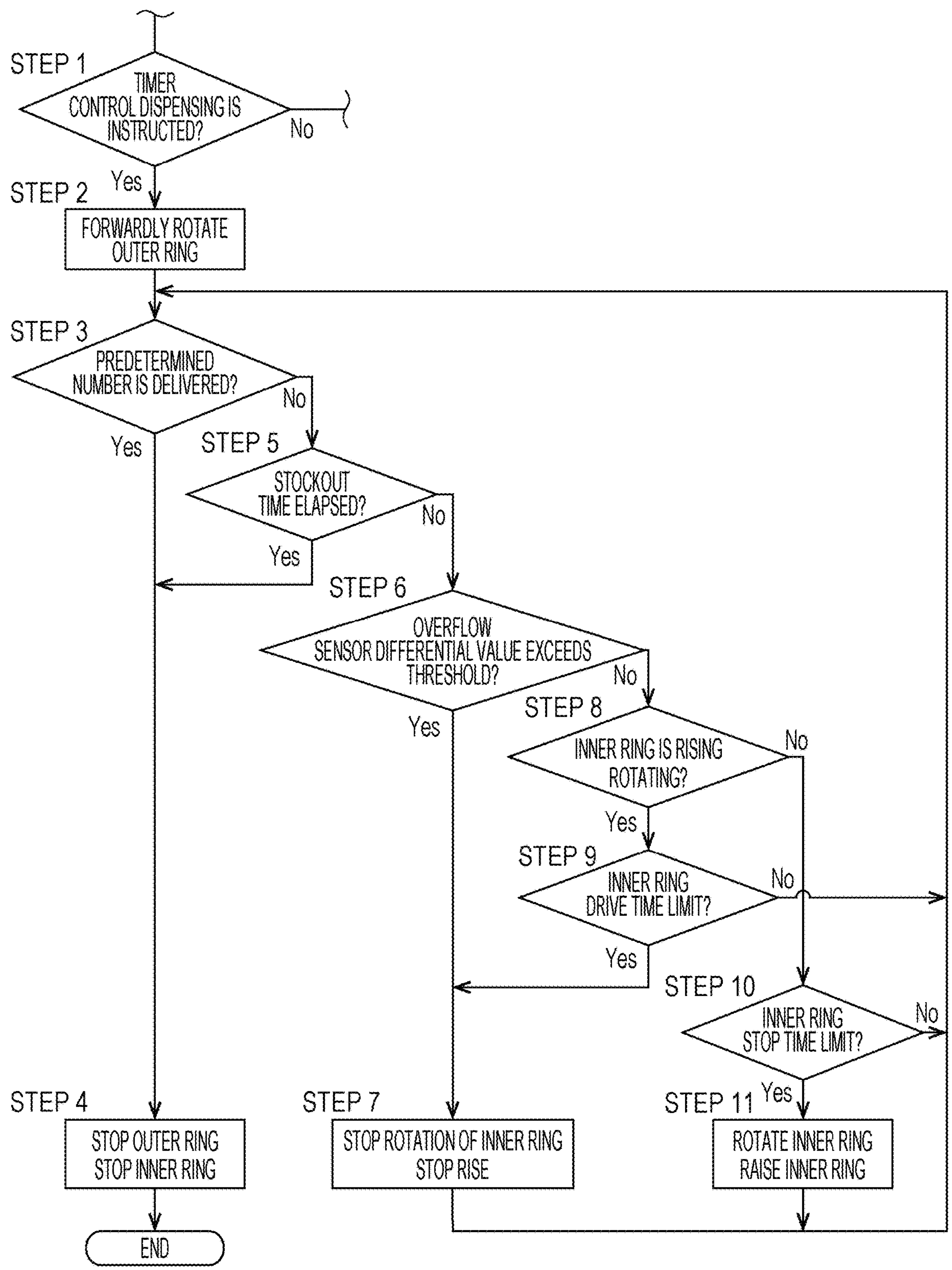
FIG. 21 is a flowchart for illustrating a part of the operation of the drug dispensing device, and is an illustration of an operation of dispensing a tablet from the drug cassette through a timer control operation.

In the drug dispensing device 1 according to this embodiment, an operation to be performed at the time of dispensing tablets from the drug cassette 10 through the timer-control dispensing operation is as illustrated in a flowchart of FIG. 21. A flow of the timer-control dispensing operation is the same as that of the normal dispensing operation of FIG. 20 up to Step 5. In the timer-control dispensing operation, it is determined in Step 6 whether or not the quantity of light exceeds the threshold of the differential value.

When the quantity of light exceeds the threshold of the differential value, the operation proceeds to Step 7, and the rise of the first rotary body 50 is stopped. Then, the operation returns to Step 3. When the quantity of light does not exceed the threshold of the differential value in Step 6, the operation proceeds to Step 8, and determination is made on whether or not the inner ring is rising. When the inner ring is rising, the operation proceeds to Step 9, and determination is made on whether or not a certain inner-ring drive time limit has been reached. When the inner-ring drive time limit has not been reached, the operation returns to Step 3. When the inner-ring drive time limit has been reached, the operation proceeds to Step 7, and the rise of the first rotary body 50 is stopped. Then, the operation returns to Step 3.

When the inner ring is not rising in Step 8, determination is made on whether or not a certain inner-ring stop time limit has been reached. When the inner-ring stop time limit has not been reached, the operation returns to Step 3. When the inner-ring stop time limit has been reached, the operation proceeds to Step 11, and the first rotary body 50 is rotated and raised.

(Sensitivity Adjustment for Overflow Sensor 53) It is preferred that the threshold of the overflow sensor 53 be moderately adjusted. In this embodiment, the adjustment of the threshold of the overflow sensor 53 is performed at the time of dispensing the drug from the drug cassette 10. Here, in this embodiment, at the time of performing the threshold adjustment for the overflow sensor 53, it is checked whether or not tablets are present on the second rotary body 51 with a current threshold. When tablets are not present on the second rotary body 51, the threshold adjustment for the overflow sensor 53 is performed.

This is because, when the threshold adjustment is performed under the state in which tablets are present on the second rotary body 51, the light is reflected on the surface of the tablets at the time of the threshold adjustment so that the threshold may be set higher. When the threshold is set higher, the first rotary body 50 rises. As a result, there is a fear in that, even though the tablets have moved from the first rotary body 50 to the second rotary body 51 so that the timing has come to stop the rise of the first rotary body 50, the tablets on the second rotary body 51 cannot be detected by the overflow sensor 53, with the result that the first rotary body 50 continuously rises to cause the tablets to flow out to the second rotary body 51.

As countermeasures against the case in which the tablets are present on the second rotary body 51, the following two main countermeasures are conceivable. As the first countermeasure, the second rotary body 51 is reversely rotated to return the tablets present on the second rotary body 51 from the second rotary body 51 to the first rotary body 50 side, and after that, the threshold adjustment for the overflow sensor 53 is performed. As the second countermeasure, the second rotary body 51 is forwardly rotated to deliver the tablets present on the second rotary body 51 from the tablet delivery port 17, and after that, the threshold adjustment for the overflow sensor 53 is performed. Now, description is given.

(First Countermeasure) The tablet delivery port 17 is provided on the second rotary body 51. When the second rotary body 51 is rotated in the forward direction, the drug is delivered from the tablet delivery port 17 to the outside. In contrast, when the second rotary body 51 is rotated in the reverse direction, the drug present on the second rotary body 51 hits a cover or the like of the tablet delivery port 17 and falls toward the first rotary body (inner ring) 50 side. Then, when tablets are not detected by the overflow sensor 53, the reverse rotation of the second rotary body 51 is stopped, and the threshold adjustment for the overflow sensor 53 is started.

As described above, in this embodiment, at the time of performing the threshold adjustment for the overflow sensor 53, it is checked that tablets are not present on the second rotary body 51, and the threshold adjustment is performed only when tablets are not present. Then, the drug is dispensed through the normal dispensing operation. Even when the reverse rotation of the second rotary body 51 is continued for a certain time period, the threshold adjustment for the overflow sensor 53 is not performed as long as tablets are continuously detected by the overflow sensor 53.

Even when the reverse rotation of the second rotary body 51 is continued for a certain time period, a method of raising the first rotary body 50 more slowly than the normal case or the time-control dispensing operation described above is performed as long as tablets are continuously detected by the overflow sensor 53.

In the former method, the first rotary body 50 is raised more slowly than the normal case. For example, the rising speed of the first rotary body 50 is limited through use of, for example, a timer. That is, the rising speed of the first rotary body 50 is suppressed so that the amount of tablets to be moved to the second rotary body 51 as a result of the rise of the first rotary body 50 becomes smaller than the amount of tablets to be delivered from the delivery port through the rotation of the second rotary body 51. According to this method, at the time of dispensing the drug, the first rotary body 50 provided on the inner side rises more slowly while rotating. The tablets placed on the first rotary body 50 move to the second rotary body 51 along with the rise of the first rotary body 50. However, the tablets do not overflow because the number of tablets which move to the second rotary body 51 per unit time is small and all of the tablets on the second rotary body 51 are delivered.

Figure 22:
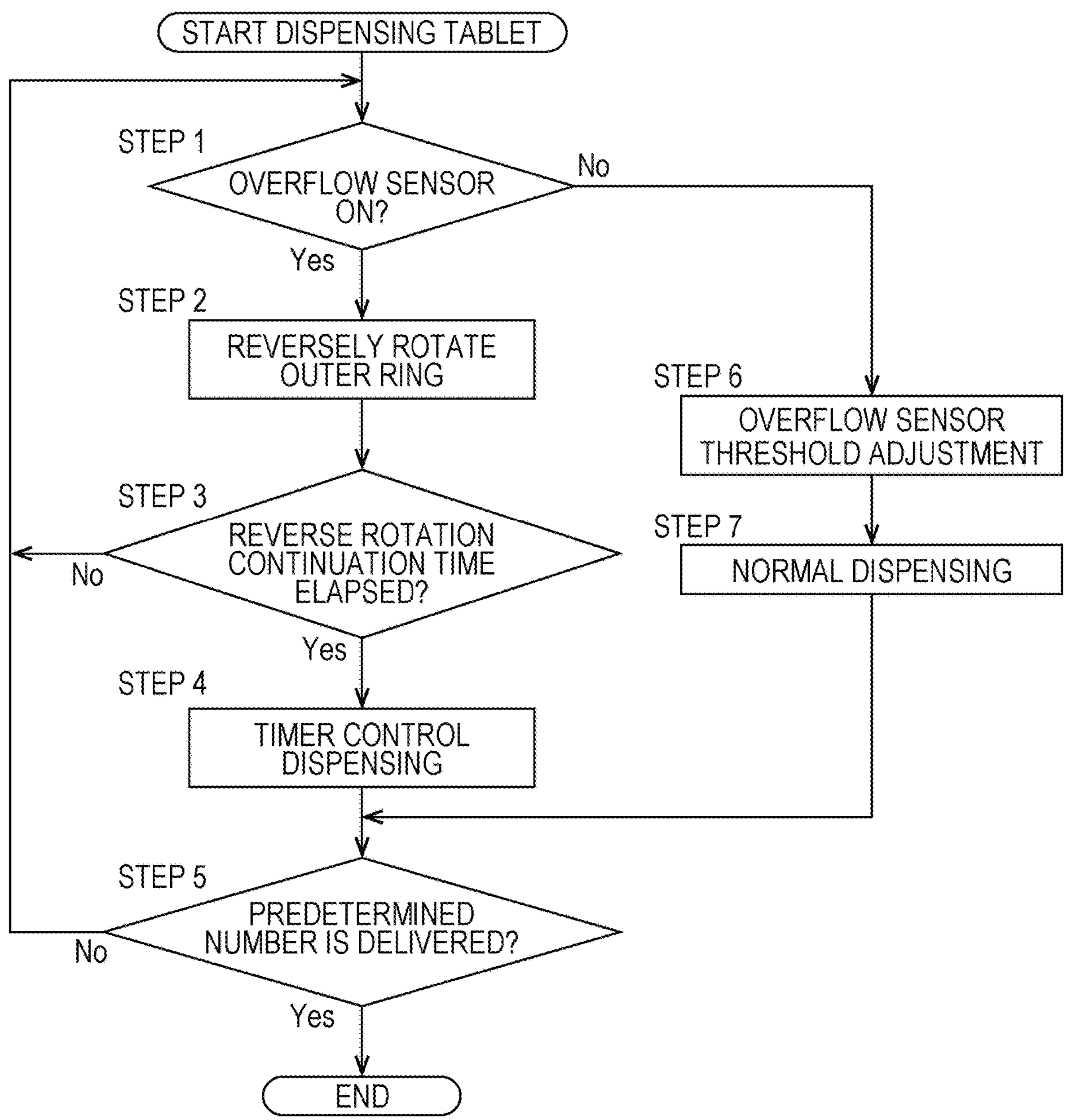
FIG. 22 is a flowchart for illustrating a part of the operation of the drug dispensing device, and is an illustration of one example of an operation of dispensing a tablet from the drug cassette.

FIG. 22 is a flowchart for illustrating the operation of reversely rotating the second rotary body 51 to return the tablets to the first rotary body 50 side in the case of using the first countermeasure. That is, in Step 1, determination is made on whether or not the drug is detected by the overflow sensor 53. In short, it is detected whether or not the drug is present on the second rotary body 51. When the drug is not present, the operation proceeds to Step 6, and the threshold adjustment for the overflow sensor 53 is performed. Then, the operation proceeds to Step 7, and the normal dispensing is performed. When the drug is present on the second rotary body 51, the operation proceeds to Step 2, and the second rotary body (outer ring) 51 is reversely rotated. In Step 3, elapse of time is determined. The second rotary body 51 is reversely rotated for a certain time period, and monitoring is performed also during that period to determine whether or not the drug is detected by the overflow sensor 53.

When the drug is not detected by the overflow sensor 53, the operation proceeds to Step 6, and the threshold adjustment for the overflow sensor 53 is performed. In a case in which the drug is detected by the overflow sensor 53 even when the second rotary body 51 reversely rotates for a certain time period, the operation proceeds to Step 4, and the timer-control dispensing operation is performed.

Moreover, after the second rotary body (outer ring) 51 is reversely rotated in Step 2, it is determined in Step 3 that a reverse-rotation continuation time has elapsed by a certain time period $\alpha 1$ while the overflow sensor 53 continues detection, and it is conceivable that determination is made on whether or not a state in which a detection signal based on a differential value of the quantity of light received by the overflow sensor 53 is not detected continues for a certain time period $\beta 1$ until the operation proceeds to the timer-control dispensing operation of Step 4. The time period $\beta 1$ to be set as the condition described above is equal to or less than the time period $\alpha 1$. That is, when the second rotary body 51 is reversely rotated, and the state in which the detection signal based on the differential value of the quantity of light received by the overflow sensor 53 is not detected under the continuation of the detection by the overflow sensor 53 continues for the certain time period $\beta 1$, the operation proceeds to Step 6, and the threshold adjustment for the overflow sensor 53 is performed. When the state in which the detection signal based on the differential value of the quantity of light received by the overflow sensor 53 is not detected under the continuation of the detection by the overflow sensor 53 does not continue for the certain time period $\beta 1$, it is determined in Step 3 that the reverse-rotation continuation time has elapsed by the certain time period $\alpha 1$ under the continuation of the detection by the overflow sensor 53. Then, the operation proceeds to Step 4, and the timer-control dispensing operation is performed. As a result, the frequency of performing the timer-control dispensing operation can be reduced.

(Second Countermeasure) In the second countermeasure, the second rotary body 51 is forwardly rotated under a state in which the first rotary body 50 is stopped, and tablets on the second rotary body 51 are delivered from the tablet delivery port 17 and charged into a vial or the like. The number of tablets charged into the vial or the like is counted by the drug counting board 402. During this operation, tablets on the second rotary body 51 are continuously monitored with the overflow sensor 53, and the rotation of the second rotary body 51 is stopped when tablets are not detected by the overflow sensor 53. Then, after that, the threshold adjustment for the overflow sensor 53 is performed. After the threshold adjustment for the overflow sensor 53 is completed, the normal tablet delivering operation is performed, thereby delivering the remaining tablets. For example, when there is a request for delivering 100 tablets in total, and six tablets are charged into the vial or the like before the threshold adjustment for the overflow sensor 53 is performed, the remaining ninety-four tablets are delivered through the normal tablet delivering operation.

Figure 23:
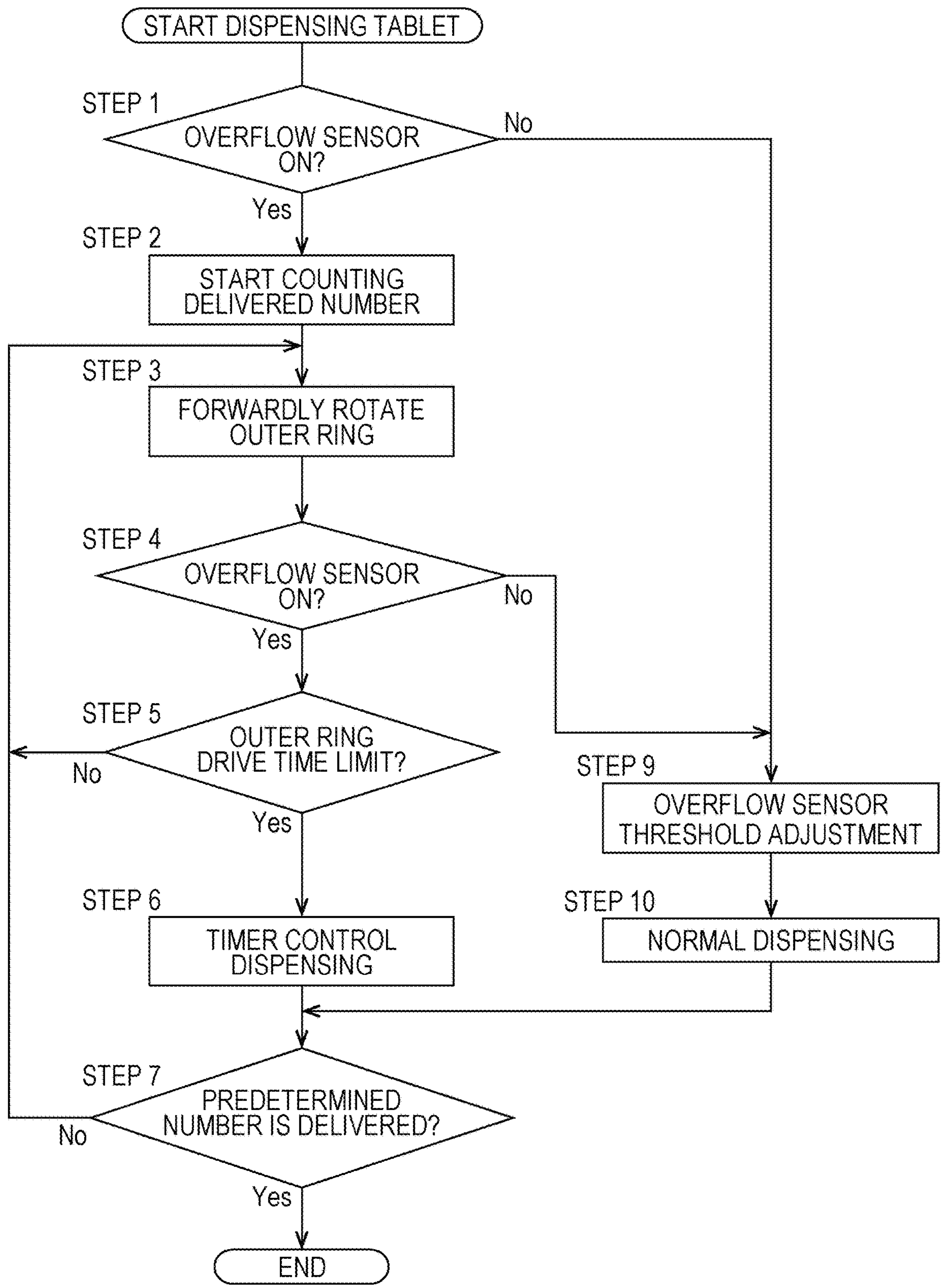
FIG. 23 is a flowchart for illustrating a part of the operation of the drug dispensing device, and is an illustration of another example of the operation of dispensing a tablet from the drug cassette.

FIG. 23 is a flowchart for illustrating the operation to be performed in the case of using the second countermeasure. That is, in Step 1, determination is made on whether or not the drug is detected by the overflow sensor 53. The operation to be performed in the case in which the drug is not present is the same as that of the first method. Thus, the operation proceeds to Step 9, and the threshold adjustment for the overflow sensor 53 is performed. Then, the operation proceeds to Step 10, and the normal dispensing is performed. When the drug is present on the second rotary body 51, the operation proceeds to Step 2, and the counting of the amount of delivery is started. Then, the operation proceeds to Step 3, and the second rotary body 51 is forwardly rotated. In Step 3, Step 4, and Step 5, the second rotary body 51 is forwardly rotated for a certain time period, and monitoring is performed also during that period to determine whether or not the drug is detected by the overflow sensor 53. When the drug is not detected by the overflow sensor 53, the operation proceeds to Step 9, and the threshold adjustment for the overflow sensor 53 is performed. In a case in which the drug is continuously detected by the overflow sensor 53 even when the second rotary body 51 is forwardly rotated for the certain time period, the operation proceeds to Step 6, and the timer-control dispensing operation is performed.

Moreover, it is conceivable that, during a period from the forward rotation of second rotary body (outer ring) 51 in Step 3 to the determination in Step 5 that the time period in which the second rotary body (outer ring) 51 forwardly rotates while the overflow sensor 53 continues the detection has elapsed by a certain time period $\alpha 2$, determination is made on whether or not a state in which a detection signal based on a differential value of the quantity of light received by the overflow sensor 53 is not detected continues for a certain time period $\beta 2$. The time period $\beta 2$ to be set as the condition described above is equal to or less than the time period $\alpha 2$. That is, when the second rotary body 51 is forwardly rotated, and the state in which the detection signal based on the differential value of the quantity of light received by the overflow sensor 53 is not detected under the continuation of the detection by the overflow sensor 53 continues for the certain time period $\beta 2$, the operation proceeds to Step 9, and the threshold adjustment for the overflow sensor 53 is performed. When the state in which the detection signal based on the differential value of the quantity of light received by the overflow sensor 53 is not detected under the continuation of the detection by the overflow sensor 53 does not continue for the certain time period $\beta 2$, the operation proceeds to Step 5. When it is determined that the time period in which the second rotary body 51 forwardly rotates under the continuation of the detection by the overflow sensor 53 has elapsed by the certain time period $\alpha 2$, the operation proceeds to Step 6, and the timer-control dispensing operation is performed. As a result, the frequency of performing the timer-control dispensing operation can be reduced.

Besides the above-mentioned example, with regard to the timing of performing the threshold adjustment for the overflow sensor 53, the threshold adjustment may be performed after tablets have been dispensed. That is, after tablets have been dispensed (after delivery of a predetermined number of tablets), the second rotary body (outer ring) 51 is reversely rotated. The second rotary body 51 is reversely rotated for a certain time period, and monitoring is performed also during that period to determine whether or not the drug is detected by the overflow sensor 53. It is conceivable to perform the threshold adjustment for the overflow sensor 53 when the drug is not detected by the overflow sensor 53 during the certain time period. Alternatively, it is conceivable to perform the threshold adjustment for the overflow sensor 53 when the state in which the detection signal based on the differential value of the quantity of light received by the overflow sensor 53 is not detected under the continuation of detection by the overflow sensor 53 continues for a certain time period.

Moreover, in any of the above-mentioned embodiments, the second rotary body (outer ring) 51 is rotated. The forward rotation and the reverse rotation may be performed alternately or at a certain ratio, and it is only required that the second rotary body 51 be finally rotated in any one of the rotation directions including the forward rotation and the reverse rotation. For example, in the second countermeasure, it is conceivable to, in Step 3, cause the second rotary body 51 to perform the forward rotation and the reverse rotation alternately or at a certain ratio and then finally perform the forward rotation.

Moreover, in a case in which the drug counting board 402 does not count the solid drug even when the second rotary body 52 is rotated for a certain time period or longer even through the overflow sensor 53 has detected that the solid drug is present in the drug cassette 10, the drug dispensing device 1 notifies a delivery error. The notification of the delivery error prompts a user to eliminate the cause of the delivery error, thereby being capable of achieving a state in which the solid drug can be delivered from the drug cassette 10. Here, as an example of the cause of the delivery error, it is conceivable that the solid drug is caught by the height regulating member 56 or the width regulating member 57. When there is any caught solid drug, a user removes it. As another example of the cause of clogging, it is conceivable that the size in the height direction to be regulated by the height regulating member 56 or the size in the width direction to be regulated by the width regulating member 57 is excessively small with respect to the solid drug. In this case, a user suitably adjusts the size to be regulated by the height regulating member 56 or the width regulating member 57.

In the drug dispensing device 1 according to this embodiment, the drug cassette 10 includes the solid-preparation receiving portion configured to receive a solid drug, the delivery port (tablet delivery port 17) configured to deliver the solid drug from the solid-preparation receiving portion, and the rotary body 51, and is configured to place the solid drug on the rotary body 51 and rotate the rotary body 51 to move the solid drug to the delivery port 17. The drug cassette 10 includes the overflow sensor 53 configured to detect whether or not the solid drug is present on the rotary body 51, and is configured to perform a sensitivity setting operation of adjusting the sensitivity of the overflow sensor 53. The sensitivity setting operation is performed under the condition in which the solid drug is not present in the rotary body 51.

Further, in the drug dispensing device 1 according to this embodiment, the drug cassette 10 includes the solid-preparation receiving portion 11 configured to receive a solid drug, the delivery port (tablet delivery port 17) configured to deliver the solid drug from the solid-preparation receiving portion 11, and the rotary body 51, and is configured to place the solid drug on the rotary body 51 and forwardly rotate the rotary body 51 to move the solid drug to the delivery port 17. The drug cassette 10 includes the overflow sensor 53 configured to detect whether or not the solid drug is present on the rotary body 51, and is configured to perform a sensitivity setting operation of adjusting the sensitivity of the overflow sensor 53. When the solid drug is present on the rotary body 51, the rotary body 51 is reversely rotated to eliminate the solid drug from the rotary body 51, and then the sensitivity setting operation is performed.

Further, in the drug dispensing device 1 according to this embodiment, the drug cassette 10 includes the solid-preparation receiving portion 11 configured to receive a solid drug, the delivery port (tablet delivery port 17) configured to deliver the solid drug from the solid-preparation receiving portion 11, and the rotary body 51, and is configured to place the solid drug on the rotary body 51 and forwardly rotate the rotary body 51 to move the solid drug to the delivery port 17. The drug cassette 10 includes the overflow sensor 53 configured to detect whether or not the solid drug is present on the rotary body 51, and is configured to perform a sensitivity setting operation of adjusting the sensitivity of the overflow sensor 53. When the solid drug is present on the rotary body 51, the rotary body 51 is forwardly rotated to deliver the solid drug from the delivery port 17, and then the sensitivity setting operation is performed.

(Light-quantity Adjustment for Drug Counting Board 402) The drug dispensing device 1 according to this embodiment includes the drug counting board 402. The drug counting board 402 includes the light-emitting side arm member 405 and the light-receiving side arm member 406. It is preferred that the quantity of light received by the light-receiving side arm member 406 fall within a certain range. Therefore, the quantity of light received by the light-receiving side arm member 406 is always monitored, and when the quantity of received light falls beyond the proper range, the light-quantity adjustment for the drug counting board 402 is performed. As described above, eight light-emitting elements (light-emitting members) 410 are mounted to the light-emitting side arm member 405. Further, the eight light-emitting elements 410 are grouped into two light-emitting-element groups 431 and 432 as surrounded by the frame. For the light-quantity adjustment, it is required that not only the total of the quantity of light emitted from the light-emitting-element groups 431 and 432 but also the balance therebetween be considered.

Therefore, the proper quantity of received light is achieved by sequentially changing combinations of the amount of power supplied to the light-emitting-element group 431 and the amount of power supplied to the light-emitting-element group 432. In this embodiment, combinations of the amount of power supplied to the light-emitting-element group 431 and the amount of power supplied to the light-emitting-element group 432 are determined in advance, and the combinations are actually tested to adjust the amount of power to an appropriate value. Moreover, the combinations of the amount of power supplied to the light-emitting-element group 431 and the amount of power supplied to the light-emitting-element group 432 are tested with priority given to combinations which often achieve appropriate values based on experience. For example, a matrix like the one illustrated in FIG. 24 is assumed, and the white outline region is set as the combinations with the first priority.

The region surrounded by an oval includes combinations which are most likely to achieve appropriate values, and the combinations of the first priority indicated by the white outline include the oval region. All of the combinations of the first priority are tested at the time of the light-quantity adjustment. That is, the combinations of the first priority fall within a standard range for testing the quantity of emitted light, and all of those combinations are tested at the time of the light-quantity adjustment. The numbers given in the table show the orders of the tests. However, all of the combinations within the standard range are tested, and hence the orders are not of the great importance. As a result of testing all of the combinations of the first priority, when there is any combination capable of obtaining the appropriate quantity of received light, the light-emitting elements 410 are caused to emit light based on the combinations.

In a case in which there is no combination capable of obtaining a preferred quantity of received light even through the combinations of the first priority are tested, other combinations are tested. In this case, as shown in the table, the orders of the tests are determined in advance, and tests are conducted in the determined order. When there is any combination capable of obtaining a preferred quantity of received light, subsequent tests are cancelled, and the light-emitting elements 410 are caused to emit light based on the combination.

The combinations may be grouped into, for example, a second priority group and a third priority group. When there is no appropriate combination among the combinations of the first priority, a method of testing all of the combinations belonging to the second priority group may be used.

It is preferred that, with regard to the light-quantity adjustment for the drug counting board 402, the tests for the combinations of the first priority be continuously conducted. However, there is discontent that the operation of dispensing the drug is suspended for a certain time period. Therefore, when there is given a new request for dispensing the drug during the light-quantity adjustment, the light-quantity adjustment may be suspended, and the operation of dispensing the drug may be performed.

In the case of suspending the light-quantity adjustment, it is preferred that data of the tests having been conducted and information as to the course of the tests be stored in storage means. Then, at the time of restarting the light-quantity adjustment, it is recommended that the overlapping tests be omitted and a test in the next order from the last test be restarted. Alternatively, combinations having been tested in the past, for example, combinations having tested last time may be tested again, and comparison may be made with the stored data. When the difference therebetween is equal to or less than a certain value, the overlapping tests may be omitted. When the difference therebetween is large, tests may be conducted from the first.

The drug dispensing device 1 according to this embodiment includes the drug counting means configured to count the number of the solid drug delivered from the drug cassette 10. The drug counting means includes the light-emitting portion (light-emitting side arm member 405) including the plurality of light-emitting elements 410 and the light-receiving portion (light-receiving side arm member 406) including the plurality of light-receiving elements 411, and is configured to perform a counter adjustment operation of appropriately adjusting the quantity of light emitted from the light-emitting portion and/or the sensitivity of the light-receiving portion under certain requirements. The light-emitting elements 410 are individually provided or are grouped into a plurality of light-emitting-element groups and are capable of adjusting the quantity of emitted light for each light-emitting-element group. Combinations of power supplied to the light-emitting elements 410 or light-emitting-element groups are set, and the combinations are grouped so as to have priority orders. All of the combinations of the power belonging to the first priority group are subjected to trial. As a result of the trial, when there is any preferred combination, the power to be supplied is set to the combination. Moreover, when there is no preferred combination, combinations of power other than the first priority order group are subjected to trial.

Moreover, the drug dispensing device 1 according to this embodiment includes the drug counting means (drug counting board 402) configured to count the number of the solid drug delivered from the drug cassette 10. The drug counting means includes the light-emitting portion (light-emitting side arm member 405) including the plurality of light-emitting elements 410 and the light-receiving portion (light-receiving side arm member 406) including the plurality of light-receiving elements 411, and is configured to perform the counter adjustment operation of appropriately adjusting the quantity of light emitted from the light-emitting portion and/or the sensitivity of the light-receiving portion under certain requirements. The light-emitting elements 410 are individually provided or are grouped into a plurality of light-emitting-element groups and are capable of adjusting the quantity of emitted light for each light-emitting-element group. Combinations of power supplied to the light-emitting elements or light-emitting-element groups are set, and all of the combinations of the power are subjected to trial in a predetermined order. The trial can be suspended. In the case of suspending the trial, trial results of specified light-emitting elements or light-emitting-element groups are stored. At the time of restarting the trial, the stored combinations and the like are subjected to trial again, and comparison is made between the stored trial results and trial results given as a result of the trial conducted again. When the difference therebetween is equal to or less than a certain value, the suspended trial is continuously conducted. When the difference therebetween exceeds the certain value, the trial is conducted again.

The invention claimed is:

1. A drug dispensing device, comprising:

a plurality of drug cassettes, wherein the drug dispensing device is configured to distribute a determined amount of solid drugs from a corresponding drug cassette of the plurality of drug cassettes, and each of the plurality of drug cassettes includes:

a solid-preparation receiving portion configured to receive a solid drug from the corresponding drug cassette; and a lid configured to close the solid-preparation receiving portion, a lid lock configured to hold the lid member in a locked state;

a cassette placement portion configured to receive a drug cassette of the plurality of drug cassettes;

a removal lock configured to selectively hold the drug cassette on the cassette placement portion and prevent removal of the drug cassette;

a lid lock operator configured to operate the lid lock, wherein the lid lock operator is configured to:

set the lid lock into a locked state or an unlocked state, maintain the lid lock in the unlocked state, in response to the lid lock being set in the unlocked state, until the lid lock operator receives an input for changing the lid lock to the locked state, and automatically set the drug cassette into a removable state permitting removal from the cassette placement portion, in response to the lid lock being set in the locked state or in response satisfying of a condition for bringing the lid lock into the locked state; and an operating portion for receiving an input from an operator, wherein the operating portion is configured to set the drug cassette into the removable state in response to receiving a predetermined input from the operator;

wherein, the operating portion is configured to receive operator information related to the operator, a date, and at least one identifying information selected from the group consisting of a drug serial number information, the number of replenishment, and an expiration date, and the lid lock operator, in response to the operator information, the date and the at least one identifying information satisfying a predetermined condition, is configured to:

set the lid lock into the locked state, and set the removal lock to permit removal of the drug cassette from the cassette placement portion.

2. The drug dispensing device according to claim 1, further comprising a storage, wherein the storage is configured to store the operator information, the date, and drug-cassette identification information in associated with the at least one identifying information.

3. A drug dispensing device, comprising:

a plurality of drug cassettes, wherein the drug dispensing device is configured to distribute a determined amount of solid drugs from a corresponding drug cassette of the plurality of drug cassettes, and each of the plurality of drug cassettes includes:

a solid-preparation receiving portion configured to receive a solid drug from the corresponding drug cassette; and a lid configured to close the solid-preparation receiving portion, a lid lock configured to hold the lid member in a locked state;

a cassette placement portion configured to receive a drug cassette of the plurality of drug cassettes;

a removal lock configured to selectively hold the drug cassette on the cassette placement portion and prevent removal of the drug cassette;

a lid lock operator configured to operate the lid lock, wherein the lid lock operator is configured to:

set the lid lock into a locked state or an unlocked state, maintain the lid lock in the unlocked state, in response to the lid lock being set in the unlocked state, until the lid lock operator receives an input for changing the lid lock to the locked state, and automatically set the drug cassette into a removable state permitting removal from the cassette placement portion, in response to the lid lock being set in the locked state or in response satisfying of a condition for bringing the lid lock into the locked state; and an operating portion, wherein, the operating portion is configured to receive operator information related to the operator, a date, and at least one identifying information selected from the group consisting of a drug serial number information, a number of replenishment, and an expiration date, and the lid lock operator, in response to the operator information, the date and the at least one identifying information satisfying a predetermined condition, is configured to:

set the lid lock into the locked state, and set the removal lock to permit removal of the drug cassette from the cassette placement portion.

4. The drug dispensing device according to claim 3, further comprising a storage, wherein the storage is configured to store the operator information, the date, and drug-cassette identification information in associated with the at least one identifying information.

5. A drug dispensing device, comprising:

a plurality of drug cassettes, wherein the drug dispensing device is configured to distribute a desired amount of solid drugs from a corresponding drug cassette of the plurality of drug cassettes, and each of the plurality of drug cassettes includes:

a solid-preparation receiving portion configured to receive a corresponding solid drug;

a lid configured to close the solid-preparation receiving portion; and lid lock configured to hold the lid member in a locked state, a lid lock operator configured to operate the lid lock, wherein the lid lock operator is configured to set the lid lock into the locked state in response to receiving a predetermined input from an operator;

a cassette placement portion configured to receive a drug cassette of the plurality of drug cassettes;

a removal lock configured to selectively hold the drug cassette on the cassette placement portion and prevent removal of the drug cassette; and an operating portion, wherein, the operating portion is configured to receive operator information related to the operator, a date, and at least one identifying information selected from the group consisting of a drug serial number information, a the number of replenishment, and an expiration date, and the lid lock operator, in response to the operator information, the date and the at least one identifying information satisfying a predetermined condition, is configured to:

set the lid lock into the locked state, and set the removal lock to permit removal of the drug cassette from the cassette placement portion.

6. The drug dispensing device according to claim 5, further comprising a storage, wherein the storage is configured to store the operator information, the date, and drug-cassette identification information in associated with the at least one identifying formation.

* * * * *